(12) United States Patent
Reisner et al.

(10) Patent No.: US 11,773,372 B2
(45) Date of Patent: *Oct. 3, 2023

(54) VETO CELLS GENERATED FROM MEMORY T CELLS

(71) Applicant: Yeda Research and Development Co. Ltd., Rehovot (IL)

(72) Inventors: Yair Reisner, Tel Aviv-Jaffa (IL); Noga Or-Geva, Rehovot (IL); Rotem Gidron Budovsky, Rehovot (IL); Esther Bachar-Lustig, Rehovot (IL); Assaf Lask, Rehovot (IL); Sivan Kagan, Rehovot (IL)

(73) Assignee: Yeda Research and Development Co. Ltd., Rehovot (IL)

(*) Notice: Subject to any disclaimer, the term of this patent is extended or adjusted under 35 U.S.C. 154(b) by 122 days.

This patent is subject to a terminal disclaimer.

(21) Appl. No.: 17/211,863

(22) Filed: Mar. 25, 2021

(65) Prior Publication Data

US 2021/0214687 A1 Jul. 15, 2021

Related U.S. Application Data

(63) Continuation of application No. 16/313,486, filed as application No. PCT/IL2017/050716 on Jun. 27, 2017, now Pat. No. 10,961,504.

(60) Provisional application No. 62/354,950, filed on Jun. 27, 2016.

(51) Int. Cl.
| | |
|---|---|
| *C12N 5/0783* | (2010.01) |
| *A61K 35/17* | (2015.01) |
| *A61K 39/00* | (2006.01) |
| *C12N 5/00* | (2006.01) |
| *A61K 35/12* | (2015.01) |

(52) U.S. Cl.
CPC ............ *C12N 5/0637* (2013.01); *A61K 35/17* (2013.01); *A61K 39/001* (2013.01); *C12N 5/0087* (2013.01); *A61K 2035/122* (2013.01); *A61K 2039/5158* (2013.01); *C12N 2501/2307* (2013.01); *C12N 2501/2315* (2013.01); *C12N 2501/2321* (2013.01); *C12N 2502/1121* (2013.01)

(58) Field of Classification Search
CPC ............... C12N 5/0637; C12N 5/0087; C12N 2501/2307; C12N 250/2315; C12N 2501/2321; C12N 2502/1121; A61K 35/17; A61K 39/001; A61K 2035/122; A61K 2039/5158; Y02A 50/30; A61P 43/00; A61P 35/04; A61P 35/02; A61P 35/00

See application file for complete search history.

(56) References Cited

U.S. PATENT DOCUMENTS

| | | |
|---|---|---|
| 2011/0212071 A1 | 9/2011 | Reisner et al. |
| 2018/0207272 A1 | 7/2018 | Reisner et al. |
| 2019/0316087 A1 | 10/2019 | Reisner et al. |

FOREIGN PATENT DOCUMENTS

| | | |
|---|---|---|
| CN | 102271702 | 12/2011 |
| CN | 103930130 | 7/2014 |
| JP | 2013-537187 | 9/2013 |
| JP | 2014-526244 | 10/2014 |
| WO | WO 01/49243 | 7/2001 |
| WO | WO 2007/023491 | 3/2007 |
| WO | WO 2010/049935 | 5/2010 |
| WO | WO 2012/032526 | 3/2012 |
| WO | WO 2013/035099 | 3/2013 |
| WO | WO 2014/151006 | 9/2014 |
| WO | WO 2018/002924 | 1/2018 |

OTHER PUBLICATIONS

Request for Examination dated Nov. 1, 2021 From the (ROSPATENT), Federal Government Institution of Industrial Property of the Federal Service of Intellectual Property, Patents and Trademark of the Russian Federation Re. Application No. 2019101826 and its Translation Into English. (6 Pages).

Dornmair et al. "T-Cell-Mediated Autoimmunity: Novel Techniques to Characterize Autoreactive T-Cell Receptors", The American Journal of Pathology,163(4):1215-1226, Oct. 2003.

Communication Pursuant to Article 94(3) EPC dated May 3, 2021 From the European Patent Office Re. Application No. 17740119.7. (7 Pages).

International Preliminary Report on Patentability dated Jan. 10, 2019 From the International Bureau of WIPO Re. Application No. PCT/IL2017/050716. (9 Pages).

International Search Report and the Written Opinion dated Oct. 9, 2017 From the International Searching Authority Re. Application No. PCT/IL2017/050716. (17 Pages).

(Continued)

*Primary Examiner* — Rachel B Gill

(57) ABSTRACT

A method of generating an isolated population of non graft versus host disease (GvHD) inducing cells comprising a central memory T-lymphocyte (Tcm) phenotype, the cells being tolerance inducing cells and/or endowed with anti-disease activity, and capable of homing to the lymph nodes following transplantation is disclosed. The method comprising: (a) providing a population of at least 70% memory T cells; (b) contacting the population of memory T cells with an antigen or antigens so as to allow enrichment of antigen reactive cells; and (c) culturing the cells resulting from step (b) in the presence of cytokines so as to allow proliferation of cells comprising the Tcm phenotype. Cells generated by the method, pharmaceutical compositions and methods of treatment are also disclosed.

21 Claims, 17 Drawing Sheets

(56) References Cited

OTHER PUBLICATIONS

Notice of Reasons for Refusal dated Mar. 17, 2021 From the Japan Patent Office Re. Application No. 2018-567129. (6 Pages).
Official Action dated May 12, 2020 From the Re. U.S. Appl. No. 16/313,486. (23 Pages).
Request for Examination dated Sep. 3, 2020 From the (ROSPATENT), Federal Government Institution of Industrial Property of the Federal Service of Intellectual Property. Patents and Trademark of the Russian Federation Re. Application No. 2019101826 and Its Translation Into English. (9 Pages).
Search Report and Written Opinion dated Sep. 4, 2019 From the Intellectual Property Office of Singapore, IPOS Re. Application No. 11201811563R. (11 Pages).
Translation Dated Apr. 7, 2021 of Notice of Reasons for Refusal dated Mar. 17, 2021 From the Japan Patent Office Re. Application No. 2018-567129. (6 Pages).
Written Opinion dated Jun. 25, 2020 From the Intellectual Property Office of Singapore, IPOS Re. Application No. 11201811563R. (7 Pages).
Anderson et al. "Memory CD4+ T Cells Do Not Induce Graft-Versus-Host Disease", The Journal of Clinical Investigation, 112(1): 101-108, Jul. 2003.
Bleakley et al. "Outcomes of Acute Leukemia Patients Transplanted With Naive T Cell-Depleted Stem Cell Grafts", The Journal of Clinical Investigation, XP055409564, 125(7): 2677-2689, Jul. 2015.
Chen et al. "Inability of Memory T Cells to Induce Graft-Versus-Host Disease Is A Result of An Abortive Alloresponse", Blood, XP055410126, 109(7): 3115-3123, Pubhshed Online Dec. 5, 2006.
Gattinoni et al. "T Memory Stem Cells in Health and Disease", Nature Medicine, 23(1): 18-27, Jan. 6, 2017.
Juchem et al. "A Repertoire-Independent and Cell-Intrinsic Defect in Murine GVHD Induction by Effector Memory T Cells", Blood, 118(23): 6209-6219, Pubhshed Online Jul. 18, 2011.
Lee et al. "Depletion of Alloreactive T-Cells by Anti-CD137-Saporin Immunotoxin", Cell Transplantation, 24(6): 1167-1181, Published Online Mar. 3, 2014.
Ophir et al. "Induction of Tolerance to Bone Marrow Allografts by Donor-Derived Host Nonreactive Ex Vivo Induced Central Memory CD8 T Cells", Blood, XP009165643, 115(10): 2095-2104, Mar. 11, 2010. p. 1221, 1-h Col., p. 1226, r-h col. Para 2-3.
Ophir et al. "Murine Anti-Third-Party Central-Memory CD8+ T Cells Promote Hematopoietic Chimerism Under Mild Conditioning: Lymph-Node Sequestration and Deletion of Anti-Donor T Cells", Blood, XP055409570, 121(7): 1220-1228, Published Online Dec. 5, 2012.
Or-Geva et al. "The Role of Donor-Derived Veto Cells in Nonmyeloablative Haploidentical HSCT", Bone Marrow Transplantation, 50(Suppl. 2): S14-S20, Jun. 3, 2015.
Teschner et al. "Depletion of Naive T Cells Using Clinical Grade Magnetic CD45RA Beads: A New Approach for GVHD Prophylaxis". Bone Marrow Transplantation, 49(1): 138-144, Published Online Aug. 12, 2013.
Triplett et al. "Rapid Memory T-Cell Reconstitution Recapitulating CD45RA-Depleted Haploidentical Transplant Graft Content in Patients With Hematologic Malignancies", Bone Marrow Transplant, XP055409568, 50(7): 968-977, Pubhshed Online Feb. 9, 2015.
Zheng et al. "Central Memory CD8+ T Cells Induce Graft-Versus-Host Disease and Mediate Graft-Versus-Leukemia", The Journal of Immunology, XP055409561, 182(10): 5938-5948, May 15, 2009.
Communication Pursuant to Article 94(3) EPC dated Sep. 9, 2022 From the European Patent Office Re. Application No. 17740119.7. (7 Pages).
English Translation Dated Feb. 14, 2022 of Notification of Office Action and Search Report dated Jan. 6, 2022 From the State Intellectual Property Office of the People's Republic of China Re. Application No. 201780052593.8. (112 Pages).
Notification of Office Action and Search Report dated Jan. 6, 2022 From the State Intellectual Property Office of the People's Republic of China Re. Application No. 201780052593.8. (15 Pages).
Reisner et al. English Abstract, Description and Caims of Corr-responding Document WO 2013/035099.
Request for Examination dated Jun. 3, 2021 From the (ROSPATENT), Federal Government Institution of Industrial Property of the Federal Service of Intellectual Property, Patents and Trademark of the Russian Federation Re. Application No. 2019101826 and Its Translation Into English.(7 Pages).
Cieri et al. "Generation of Human Memory Stem T Cells After Haploidentical T-Replete Hematopoietic Stem Cell Transplantation", Blood, 125(18):2865-2874, Apr. 30, 2015.
Office Action dated Jul. 7, 2022 From the Israel Patent Office Re. Application No. 263924. (4 Pages).
Notice of Reason(s) for Rejection dated Jan. 18, 2023 From the Japan Patent Office Re. Application No. 2018-567129. (3 pages).
Machura et al. "Expression of Naive/Memory (CD45RA/CD45RO) Markers by Peripheral Blood CD4+ and CD8+ T Cells in Children with Asthma", Archivum Immunologiae et Therapiae Experimentalis, 56: 55-62, Feb. 5, 2008.
Translation Dated Jan. 30, 2023 of Notice of Reason(s) for Rejection dated Jan. 18, 2023 From the Japan Patent Office Re. Application No. 2018-567129. (3 pages).
Examination Report Under Sections 12 & 13 of the Patents Act. 1970 and the Patents Rules, 2003 dated Nov. 22, 2022 From the Government of India, Intellectual Property India, Patents, Designs, Trade Marks, Geographical Indications, The Patent Office Re. Application No. 201927002672.(12 pages).
Examination Report dated Oct. 28, 2022 from the Australian Patent Office Re. Application No. 2017289879. (4 pages).

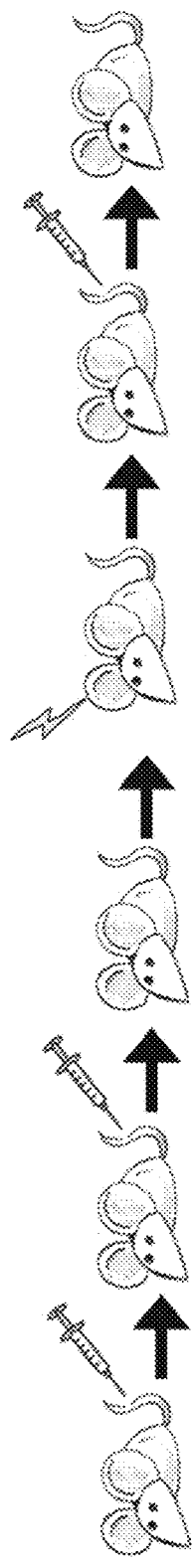

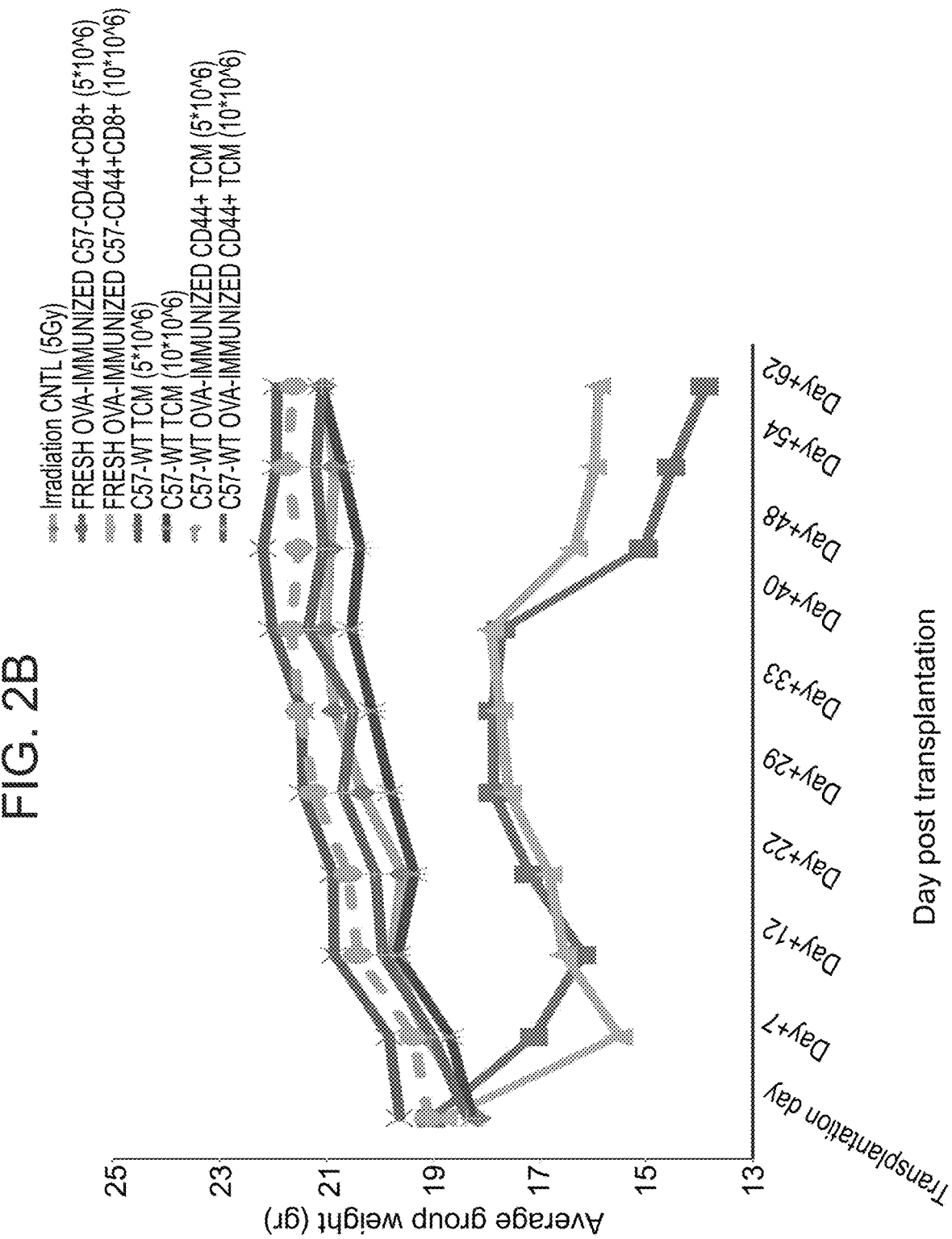

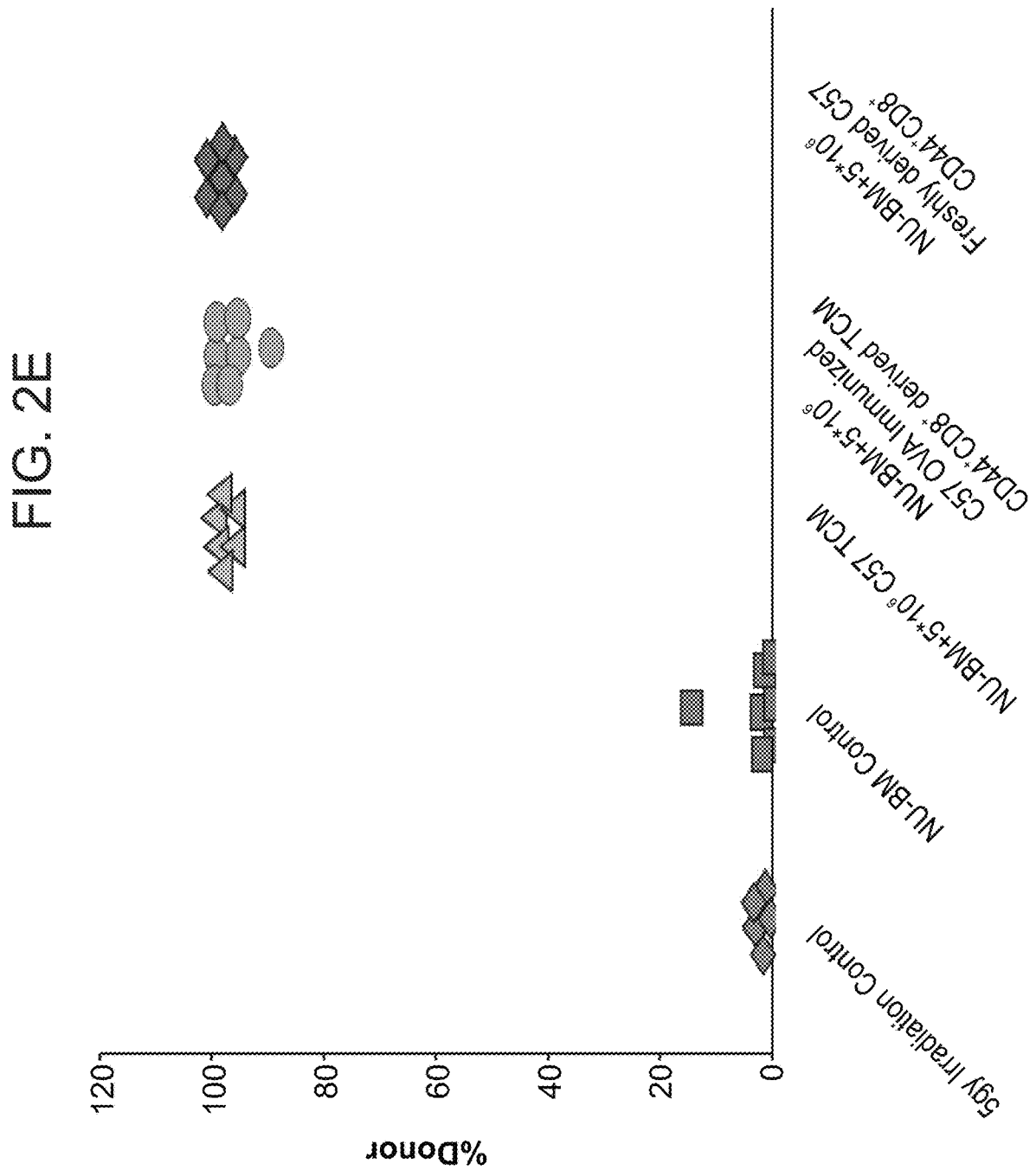

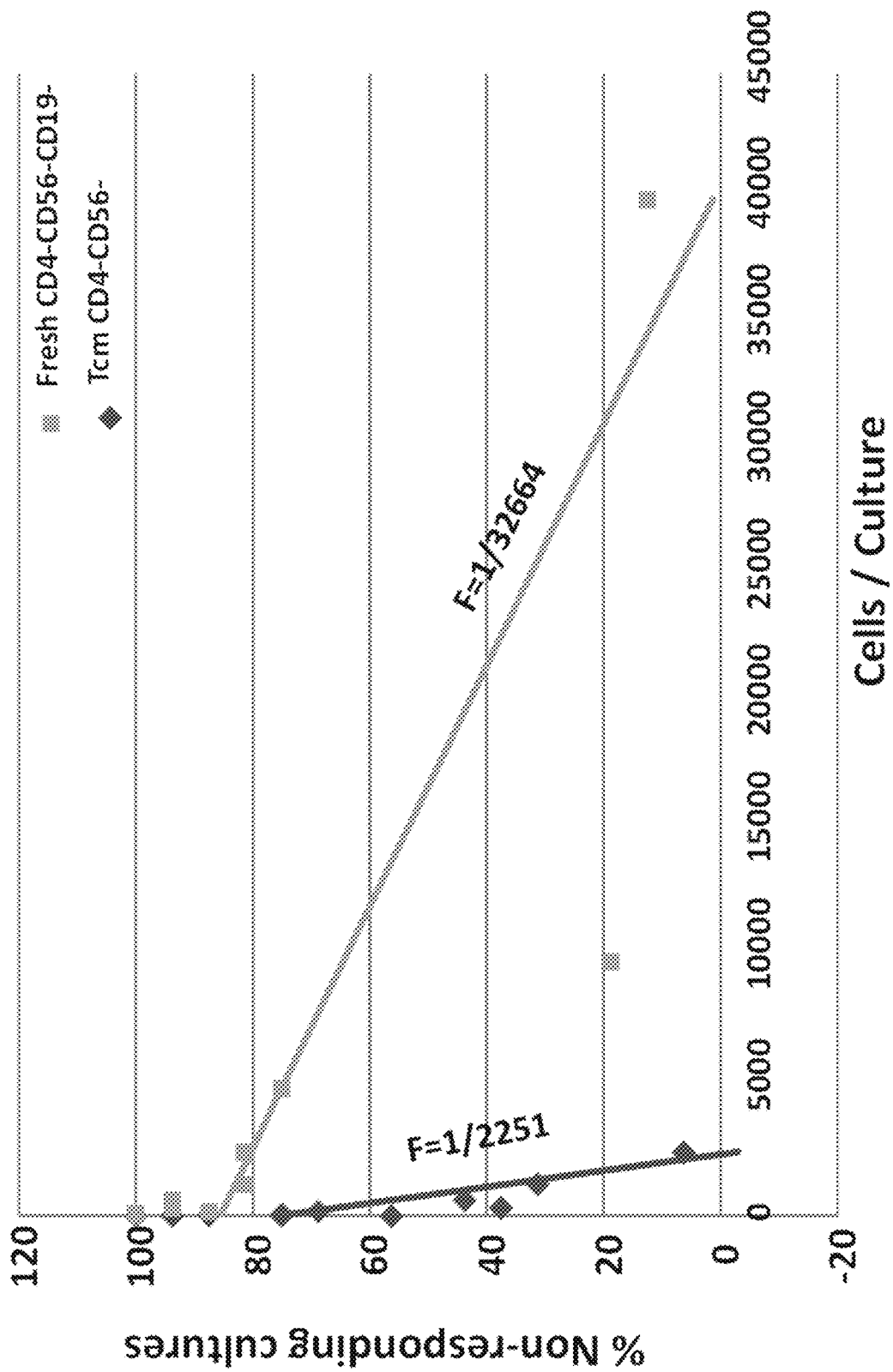

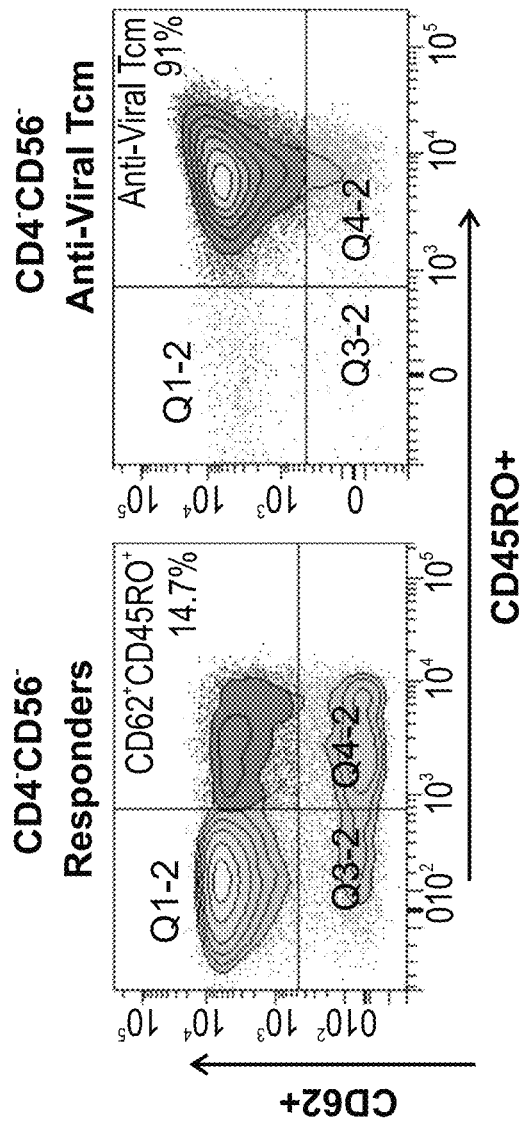
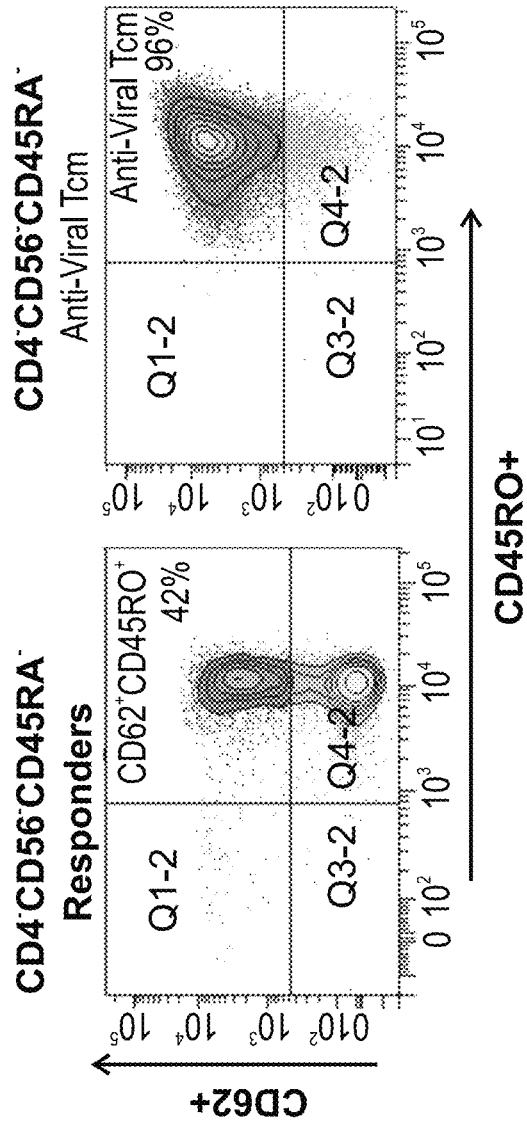
FIG. 5A
FIG. 5B

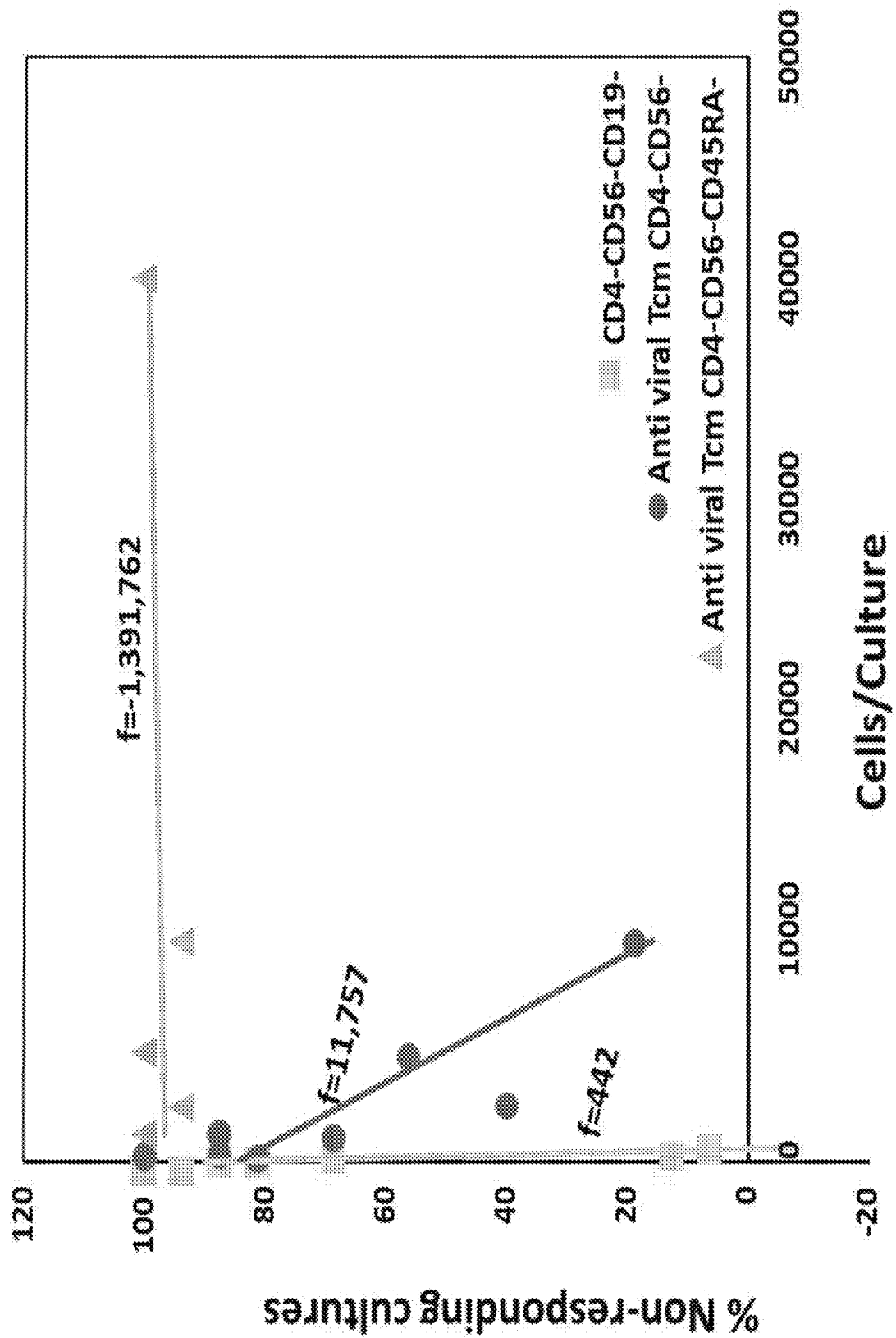

FIG. 6

| Cell Fraction | Cell number Seeded for bulk culture Vs host (Day 9) | Cell number Harvested after bulk culture (Day 14) | Anti-host CTL-p frequency based on LDA | Total anti-host CTL-p (x10⁶) based on LDA (Normalized to 100x10⁶) | Depletion factor |
|---|---|---|---|---|---|
| Fresh CD4,56,19- | 50x10⁶ | 30x10⁶ | 1/442 | 0.136 | |
| Anti-Viral Tcm CD4,56- | 200x10⁶ | 30x10⁶ | 1/11,757 | 0.00128 | 106 |
| Anti-Viral Tcm CD4,scRA- | 200x10⁶ | 60x10⁶ | 1/-1,391,762 | 0.000022 | 6181 |

|  | # Vials | Day -1 Before thawing (x10⁶) | Day -1 After thawing (x10⁶) | Day 0 After Penning (x10⁶) | Day 0 After CD4-CD56 (x10⁶) | Day 0 After CD4-CD56-RA- Cell#(x10⁶) | Day 0 After CD4-CD56-RA- % | Day 9 Anti-viral Tcm Cell#(x10⁶) | Day 9 Anti-viral Tcm % | Day 9 Fold Expansion |
|---|---|---|---|---|---|---|---|---|---|---|
| Donor A (AV of 3 Exp) Total Cell # | 32 | 3167 | 2308 | 1083 | 462 | 26 | 67 | 1158 | 94 | |
| Donor B (AV of 2 Exp) Total Cell # | 22 | 2200 | 1450 | 1000 | 400 | 78 | 24 | 404 | 86 | |
| Donor C (AV of 2 Exp) Total Cell # | 30 | 3000 | 2025 | 1150 | 325 | 67 | 25 | 338 | 92 | |
| Donor D (1 Exp) Total Cell # | 30 | 3000 | 2120 | 1000 | 276 | 58 | 53 | 583 | 94 | |
| Donor E (AV of 2 Exp) Total Cell # | 30 | 2950 | 1943 | 1300 | 340 | 47 | 30 | 783 | 93 | |
| Average | 29 | 2863 | 1969 | 1107 | 361 | 55 | 40 | 653 | 92 | 11.8 |
| SD | 4 | 380 | 321 | 125 | 72 | 20 | 19 | 331 | 3 | |
| Donor A (AV of 3 Exp) Cell # of CD3+CD8+ fraction | | | | | | 17 | 67 | 1088 | 94 | |
| Donor B (AV of 2 Exp) Cell # of CD3+CD8+ fraction | | | | | | 19 | 24 | 349 | 86 | |
| Donor C (AV of 2 Exp) Cell # of CD3+CD8+ fraction | | | | | | 16 | 25 | 318 | 92 | |
| Donor D (1 Exp) Cell # of CD3+CD8+ fraction | | | | | | 31 | 53 | 550 | 94 | |
| Donor E (AV of 2 Exp) Cell # of CD3+CD8+ fraction | | | | | | 14 | 30 | 731 | 93 | |
| Average | | | | | | 19 | 40 | 607 | 92 | 31.5 |
| SD | | | | | | 7 | 19 | 310 | 3 | |
| Donor A (AV of 3 Exp) Cell # of CD62L+CD45RO+ fraction | | | | | | 7 | 27 | 897 | 77 | |
| Donor B (AV of 2 Exp) Cell # of CD62L+CD45RO+ fraction | | | | | | 8 | 10 | 187 | 47 | |
| Donor C (AV of 2 Exp) Cell # of CD62L+CD45RO+ fraction | | | | | | 8 | 12 | 228 | 65 | |
| Donor D (1 Exp) Cell # of CD62L+CD45RO+ fraction | | | | | | 12 | 20 | 466 | 80 | |
| Donor E (AV of 2 Exp) Cell # of CD62L+CD45RO+ fraction | | | | | | 5 | 12 | 699 | 89 | |
| Average | | | | | | 8 | 16 | 495 | 72 | 63.8 |
| SD | | | | | | 2 | 7 | 304 | 16 | |

FIG. 8

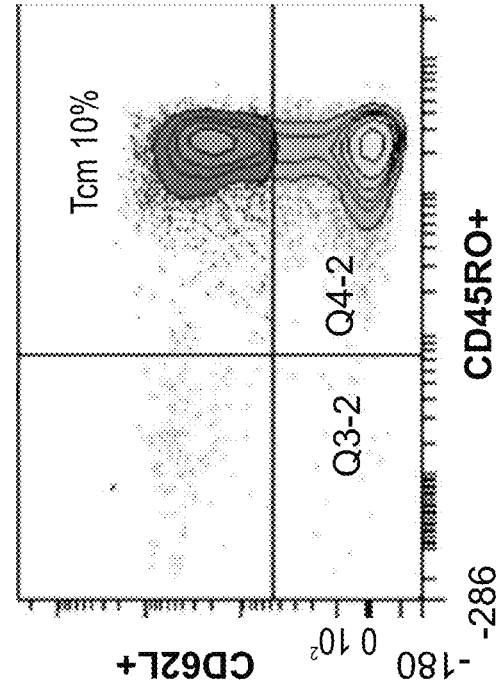
FIG. 9E After CD4-CD56-CD45RA- purification
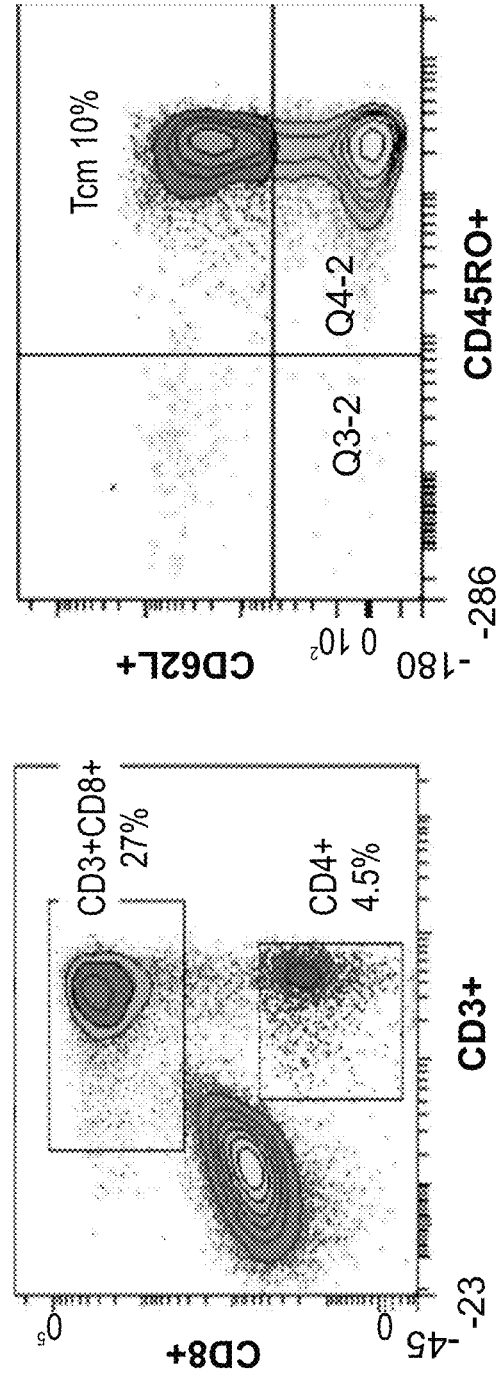
FIG. 9F
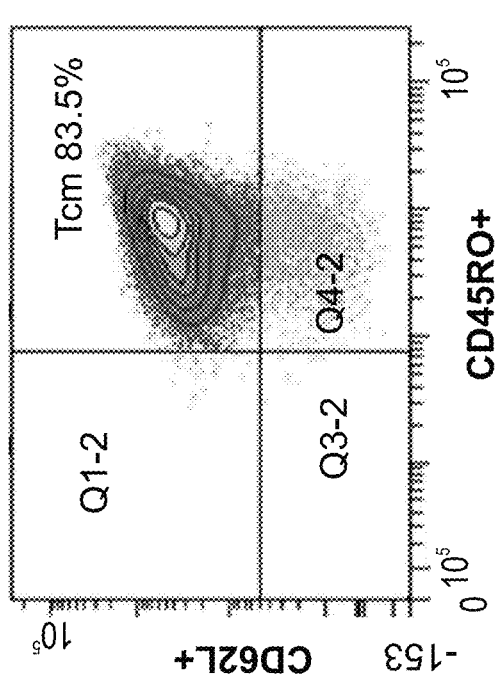
FIG. 9G Anti-Viral Tcm
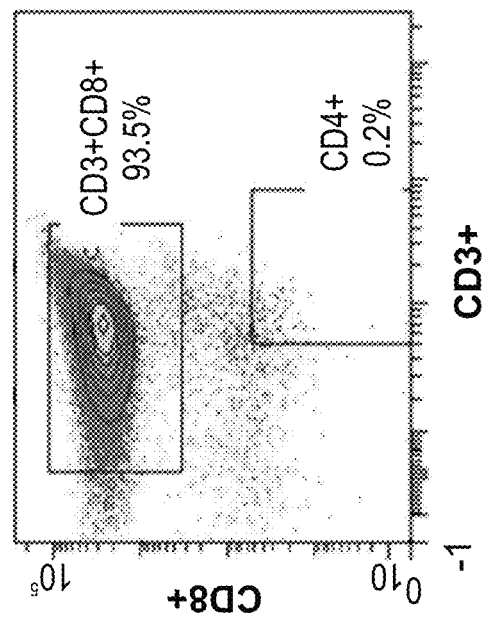
FIG. 9H

VETO CELLS GENERATED FROM MEMORY T CELLS

RELATED APPLICATIONS

This application is a Continuation of U.S. patent application Ser. No. 16/313,486 filed on Dec. 27, 2018, which is a National Phase of PCT Patent Application No. PCT/IL2017/050716 having International Filing Date of Jun. 27, 2017, which claims the benefit of priority under 35 USC § 119(e) of U.S. Provisional Patent Application No. 62/354,950 filed on Jun. 27, 2016. The contents of the above applications are all incorporated by reference as if fully set forth herein in their entirety.

FIELD AND BACKGROUND OF THE INVENTION

The present invention, in some embodiments thereof, relates to veto cells generated from memory T cells and, more particularly, but not exclusively, to methods of their manufacture and to the use of same in transplantation and in disease treatment.

Accumulating evidence has shown that in humans, CD45RA-depleted peripheral blood mononuclear cells (PBMCs) exhibit reduced graft versus host (GvH) reactivity. The premise of this approach relates to the down regulation of CD45RA expression on antigen experienced T-cells, hence by depleting CD45RA$^+$ cells, naïve T-cells are eliminated while functional antigen experienced cells, including memory T-cells, are retained. Consequentially, risk for graft versus host disease (GvHD) is markedly reduced and engraftment, immune reconstitution and graft versus leukemia/lymphoma (GvL) are enhanced relative to approaches using T cell-depleted stem cell (TCD) transplantation alone. Additionally, T regulatory cells (Treg) also belong to the CD45RA$^-$ population and may possibly contribute to the tolerogenic effects demonstrated by this cell preparation. This approach is based on preclinical studies demonstrating that mouse CD4 memory T-cells, as well as effector memory CD8 T-cells, are devoid of graft versus host (GvH) reactivity [Anderson B E et al. *J Clin Invest* (2003) 112(1):101-8].

However, Zheng et al. [Zheng H. et al. *Immunol.* (2009) 182(10):5938-48] demonstrated that CD8$^+$ central memory T-cells ($T_{cm}$) exhibited significant, albeit somewhat reduced, GvHD compared to naïve T-cells. Considering that this reduced GvHD might be associated with reduced frequency of alloreactive clones in the antigen experienced pool of memory T-cells, Juchem et al. further interrogated the possible intrinsic differences between naïve and memory T-cells that expressed similar levels of a TCR transgene directed against an antigenic peptide which is ubiquitously expressed in the recipient [Juchem K W et al. Blood. (2011) 118(23): 6209-19]. This study demonstrated that while effector memory T-cells ($T_{em}$) display low GvH reactivity, perhaps due to different homing patterns and/or the differential ability of these cells to secrete INFγ, $T_{cm}$ exhibit high GvH reactivity, comparable to that of naïve T-cells [Juchem K W. (2011), supra].

Recently, two major studies attempted to use CD45RA$^+$ depleted hematopoietic stem cell transplantation (HSCT) in leukemia patients [Bleakley M. et al. J Clin Invest. (2015) 125(7):2677-89; Triplett, B. M. et al. Bone Marrow Transplant. (2015) 50(7):968-977], however, GvHD occurrences were not completely eliminated. This could be due to the large number of infused CD45RA$^+$ T-cells and the fact that CD45RA-depleted fraction contained both $T_{cm}$ and $T_{cm}$, without regard to the preclinical data that clearly showed $T_{cm}$ to be potent inducers of GvHD.

Anti-third party donor-derived central-memory CD8$^+$ T-cells (veto Tcm) have been previously shown to support allogeneic T-cell depleted bone marrow transplant (TDBMT) engraftment under non-myeloablative reduced conditioning, resulting in tolerance induction to donor-type organs grafts, without causing GvHD [Ophir, E. et al. Blood. (2013) 121(7):1220-1228].

Furthermore, various approaches have been contemplated for generation of tolerance inducing cells (e.g. veto cells) devoid of GvH reactivity and the use of same as an adjuvant treatment for graft transplantation, some are summarized infra.

PCT Publication No. WO 2001/49243 discloses a method of transplanting a transplant derived from a donor into a recipient, the method comprises the steps of (a) transplanting the transplant into the recipient; and (b) administering to the recipient a dose including non-alloreactive anti-third party cytotoxic T-lymphocytes (CTLs), wherein the non-alloreactive anti-third party CTLs are generated by directing T-lymphocytes of the donor against a third party antigen or antigens (in the absence of exogenous IL-2), the dose being substantially depleted of T-lymphocytes (e.g. CD4$^+$ T cells and/or CD56$^+$ natural killer cells) capable of developing into alloreactive CTLs, thereby preventing or ameliorating both graft rejection by the recipient and graft versus host disease.

PCT Publication No. WO 2007/023491 discloses the use of tolerogenic cells for reducing or preventing graft rejection of a non-syngeneic graft in a subject. The tolerogenic T regulatory cells disclosed (e.g. CD4$^+$CD25$^+$ cells) may be derived from any donor who is non-syngeneic with both the subject and the graft ("third-party" tolerogenic cells). The graft (e.g. bone marrow) may be derived from any graft donor who is allogeneic or xenogeneic with the subject.

PCT Publication No. WO 2010/049935 discloses an isolated population of cells comprising non-GvHD inducing anti-third party cells having a central memory T-lymphocyte (Tcm) phenotype, the cells being tolerance-inducing cells and capable of homing to the lymph nodes following transplantation. According to WO 2010/049935 the cells are generated by: (a) contacting non-syngeneic peripheral blood mononuclear cells (PBMC) with a third party antigen or antigens under conditions which allow elimination of GVH reactive cells (e.g. a culture deprived of cytokines); and (b) culturing the cells resulting from step (a) in the presence of IL-15 under conditions which allow proliferation of cells comprising the Tcm phenotype (e.g. in the presence of IL-7 and/or IL-21).

PCT Publication No. WO 2012/032526 discloses a method of treating a disease in a subject comprising: (a) transplanting a non-syngeneic cell or tissue graft to the subject; and (b) administering to the subject a therapeutically effective amount of an isolated population of cells comprising non-graft versus host (GvHD) inducing anti-third party cells having a central memory T-lymphocyte (Tcm) phenotype, the cells being tolerance-inducing cells and capable of homing to the lymph nodes following transplantation. According to WO 2012/032526, the cells are generated by generated by: (a) contacting PBMCs with a third party antigen or antigens in the presence or absence of IL-21 under conditions which allow elimination of GVH reactive cells (e.g. culturing for 1-5 days); and (b) culturing the cells resulting from step (a) in the presence of IL-15 in an antigen free environment under conditions which allow proliferation of cells comprising the Tcm phenotype (e.g. further in the presence of IL-7).

PCT Publication No. WO 2013/035099 discloses new methods of generating an isolated population of cells comprising anti-third party cells having central memory a T-lymphocyte (Tcm) phenotype, the cells being tolerance-inducing cells and/or endowed with anti-disease activity, and capable of homing to the lymph nodes following transplantation. According to WO 2013/035099, the cells are generated by: (a) contacting PBMCs with a third party antigen or antigens in the presence of IL-21 so as to allow enrichment of antigen reactive cells; and (b) culturing the cells resulting from step (a) in the presence of IL-21, IL-15 and IL-7 in an antigen free environment so as to allow proliferation of cells comprising the Tcm phenotype.

SUMMARY OF THE INVENTION

According to an aspect of some embodiments of the present invention there is provided a method of generating an isolated population of non graft versus host disease (GvHD) inducing cells comprising a central memory T-lymphocyte (Tcm) phenotype, the cells being tolerance inducing cells and/or endowed with anti-disease activity, and capable of homing to the lymph nodes following transplantation, the method comprising: (a) providing a population of at least 70% memory T cells; (b) contacting the population of memory T cells with an antigen or antigens so as to allow enrichment of antigen reactive cells; and (c) culturing the cells resulting from step (b) in the presence of cytokines so as to allow proliferation of cells comprising the Tcm phenotype, thereby generating the isolated population of non-GvHD inducing cells.

According to an aspect of some embodiments of the present invention there is provided a method of generating an isolated population of non-GvHD inducing cells comprising a central memory T-lymphocyte (Tcm) phenotype, the cells being tolerance inducing cells and/or endowed with anti-disease activity, and capable of homing to the lymph nodes following transplantation, the method comprising: (a) treating non-adherent peripheral blood mononuclear cells (PBMCs) with an agent capable of depleting $CD4^+$, $CD56^+$ and $CD45RA^+$ cells so as to obtain a population of memory T cells comprising a $CD45RA^-CD8^+$ phenotype; (b) contacting the population of memory T cells with an antigen or antigens in the presence of IL-21 so as to allow enrichment of antigen reactive cells; and (c) culturing the cells resulting from step (b) in the presence of IL-21, IL-15 and/or IL-7 so as to allow proliferation of cells comprising the Tcm phenotype, thereby generating the isolated population of non-GvHD inducing cells.

According to an aspect of some embodiments of the present invention there is provided a method of generating an isolated population of non-GvHD inducing cells comprising a central memory T-lymphocyte (Tcm) phenotype, the cells being tolerance inducing cells and/or endowed with anti-disease activity, and capable of homing to the lymph nodes following transplantation, the method comprising: (a) treating non-adherent peripheral blood mononuclear cells (PBMCs) with an agent capable of depleting $CD4^+$, $CD56^+$ and $CD45RA^+$ cells so as to obtain a population of memory T cells comprising a $CD45RA^-$ $CD8^+$ phenotype; (b) contacting the population of memory T cells with a viral antigen or antigens in the presence of IL-21 so as to allow enrichment of antigen reactive cells; and (c) culturing the cells resulting from step (b) in the presence of IL-21, IL-15 and/or IL-7 so as to allow proliferation of cells comprising the Tcm phenotype, thereby generating the isolated population of non-GvHD inducing cells.

According to an aspect of some embodiments of the present invention there is provided an isolated population of non-GvHD inducing cells comprising cells having a central memory T-lymphocyte (Tcm) phenotype, the cells being tolerance inducing cells and/or endowed with anti-disease activity, and capable of homing to the lymph nodes following transplantation, generated according to the method of some embodiments of the invention.

According to an aspect of some embodiments of the present invention there is provided a pharmaceutical composition comprising as an active ingredient the isolated population of non-GvHD inducing cells of some embodiments of the invention and a pharmaceutical acceptable carrier.

According to an aspect of some embodiments of the present invention there is provided a method of treating a disease in a subject in need thereof, the method comprising administering to the subject a therapeutically effective amount of the isolated population of non-GvHD inducing cells of some embodiments of the invention, thereby treating the disease in the subject.

According to an aspect of some embodiments of the present invention there is provided a use of the isolated population of non-GvHD inducing cells of some embodiments of the invention for the manufacture of a medicament identified for treating a disease in a subject in need thereof.

According to an aspect of some embodiments of the present invention there is provided a method of treating a disease in a subject in need thereof, the method comprising: (a) analyzing a biological sample of a subject for the presence of an antigen or antigens associated with the disease; (b) generating an isolated population of non-GvHD inducing cells according to the method of some embodiments of the invention towards the antigen or antigens associated with the disease so as to allow enrichment of antigen reactive cells; and (c) administering to the subject a therapeutically effective amount of the isolated population of non-GvHD inducing cells of (b), thereby treating the disease in the subject.

According to an aspect of some embodiments of the present invention there is provided a method of treating a subject in need of a cell or tissue transplantation, the method comprising: (a) transplanting a cell or tissue transplant into the subject; and (b) administering to the subject a therapeutically effective amount of the isolated population of non-GvHD inducing cells of some embodiments of the invention, thereby treating the subject in need of the cell or tissue transplantation.

According to an aspect of some embodiments of the present invention there is provided a use of the isolated population of non-GvHD inducing cells of some embodiments of the invention for the manufacture of a medicament identified as an adjuvant treatment for a cell or tissue transplant into a subject, wherein the subject is in need of a cell or tissue transplantation.

According to some embodiments of the invention, the memory T cells are devoid of $CD45RA^+$ cells.

According to some embodiments of the invention, the memory T cells are devoid of $CD4^+$ and/or $CD56^+$ cells.

According to some embodiments of the invention, the contacting the population of memory T cells with an antigen or antigens in effected in the presence of IL-21.

According to some embodiments of the invention, the culturing the cells resulting from step (b) in the presence of cytokines comprises culturing the cells in the presence of any of IL-21, IL-15 and/or IL-7.

According to some embodiments of the invention, the method further comprises treating a cell donor with an antigen or antigens prior to providing the population of at least 70% memory T cells.

According to some embodiments of the invention, the population of at least 70% memory T cells are enriched towards the antigen or antigens.

According to some embodiments of the invention, the antigen or antigens is selected from the group consisting of a viral antigen, a bacterial antigen, a tumor antigen, an autoimmune disease related antigen, a protein extract, a purified protein and a synthetic peptide.

According to some embodiments of the invention, the antigen or antigens is presented by autologous antigen presenting cells, non-autologous antigen presenting cells, artificial vehicles or artificial antigen presenting cells.

According to some embodiments of the invention, the antigen or antigens is presented by antigen presenting cells of the same origin as the memory T cells.

According to some embodiments of the invention, the viral antigen or antigens is presented by autologous antigen presenting cells, non-autologous antigen presenting cells, artificial vehicles or artificial antigen presenting cells.

According to some embodiments of the invention, the viral antigen or antigens is presented by antigen presenting cells of the same origin as the PBMCs.

According to some embodiments of the invention, the antigen presenting cells are dendritic cells.

According to some embodiments of the invention, the viral antigen or antigens comprises two or more viral peptides.

According to some embodiments of the invention, the viral antigen or antigens comprises an EBV peptide, a CMV peptide and/or an Adenovirus (Adv) peptide.

According to some embodiments of the invention, the viral antigen or antigens comprises three EBV peptides, two CMV peptides and two Adenovirus (Adv) peptides.

According to some embodiments of the invention, the viral antigen or antigens is selected from the group consisting of EBV-LMP2, EBV-BZLF1, EBV-EBNA1, CMV-pp65, CMV-IE-1, Adv-penton and Adv-hexon.

According to some embodiments of the invention, the viral antigen or antigens comprises two or more of EBV-LMP2, EBV-BZLF1, EBV-EBNA1, CMV-pp65, CMV-IE-1, Adv-penton and Adv-hexon.

According to some embodiments of the invention, the viral antigen or antigens further comprises a bacterial antigen.

According to some embodiments of the invention, contacting the population of memory T cells with the antigen or antigens in the presence of the IL-21 is effected for 12 hours to 5 days.

According to some embodiments of the invention, contacting the population of memory T cells with the antigen or antigens in the presence of the IL-21 is effected for 3 days.

According to some embodiments of the invention, culturing the cells resulting from step (b) in the presence of IL-21, IL-15 and/or IL-7 is effected for 12 hours to 10 days.

According to some embodiments of the invention, culturing the cells resulting from step (b) in the presence of IL-21, IL-15 and IL-7 is effected for 4 days to 8 days.

According to some embodiments of the invention, culturing the cells resulting from step (b) in the presence of IL-21, IL-15 and IL-7 is effected for 6 days.

According to some embodiments of the invention, the total length of time for generating the non-GvHD inducing cells is 10 days.

According to some embodiments of the invention, the method further comprises depleting alloreactive cells following step (c).

According to some embodiments of the invention, depleting the alloreactive cells is effected by depletion of $CD137^+$ and/or $CD25^+$ cells following contacting the cells comprising the Tcm phenotype with host antigen presenting cells (APCs).

According to some embodiments of the invention, the method is effected ex-vivo.

According to some embodiments of the invention, the PBMCs are non-syngeneic with respect to a subject.

According to some embodiments of the invention, the PBMCs are allogeneic with respect to a subject.

According to some embodiments of the invention, the cells having the T central memory phenotype comprise a $CD3^+$, $CD8^+$, $CD62L^+$, $CD45RA^-$, $CD45RO^+$ signature.

According to some embodiments of the invention, the biological sample is selected from the group consisting of blood, plasma, serum, spinal fluid, lymph fluid and tissue biopsy.

According to some embodiments of the invention, the antigen or antigens is selected from the group consisting of a viral antigen, a bacterial antigen, a tumor antigen, and an autoimmune disease related antigen.

According to some embodiments of the invention, the method further comprises transplanting a cell or tissue transplant into the subject.

According to some embodiments of the invention, the medicament further comprises a cell or tissue transplant.

According to some embodiments of the invention, the transplanting is effected concomitantly with, prior to, or following the administering of the isolated population of non-GvHD inducing cells.

According to some embodiments of the invention, the disease is a malignant disease.

According to some embodiments of the invention, the disease is a non-malignant disease.

According to some embodiments of the invention, the isolated population of non-GvHD inducing cells are for administration prior to, concomitantly with, or following the cell or tissue transplant.

According to some embodiments of the invention, (b) is effected prior to (a) in the method of some embodiments of the invention.

According to some embodiments of the invention, (a) and (b) are effected concomitantly in the method of some embodiments of the invention.

According to some embodiments of the invention, the method further comprises conditioning the subject under sublethal, lethal or supralethal conditions prior to the transplanting.

According to some embodiments of the invention, the use of the isolated population of non-GvHD inducing cells further comprises a sublethal, lethal or supralethal conditioning protocol.

According to some embodiments of the invention, the sublethal, lethal or supralethal conditioning is selected from the group consisting of a total body irradiation (TBI), a partial body irradiation, a myeloablative conditioning, a non-myeloablative conditioning, a co-stimulatory blockade, a chemotherapeutic agent and an antibody immunotherapy.

According to some embodiments of the invention, the cell or tissue transplant is non-syngeneic with the subject.

According to some embodiments of the invention, the cell or tissue transplant and the isolated population of non-GvHD inducing cells are obtained from the same donor.

According to some embodiments of the invention, the cell or tissue transplant is derived from a donor selected from the group consisting of an HLA identical allogeneic donor, an HLA non-identical allogeneic donor and a xenogeneic donor.

According to some embodiments of the invention, the cell or tissue transplant comprises immature hematopoietic cells.

According to some embodiments of the invention, the cell or tissue transplant is selected from the group consisting of a liver, a pancreas, a spleen, a kidney, a heart, a lung, a skin, an intestine, a brain, an ovarian and a lymphoid/hematopoietic cell or tissue.

According to some embodiments of the invention, the cell or tissue transplant comprises a co-transplantation of several organs.

According to some embodiments of the invention, the co-transplantation comprises transplantation of immature hematopoietic cells and a solid organ.

According to some embodiments of the invention, the immature hematopoietic cells and the solid organ are obtained from the same donor.

According to some embodiments of the invention, the immature hematopoietic cells are transplanted prior to, concomitantly with, or following the transplantation of the solid organ.

According to some embodiments of the invention, the subject has a malignant disease.

According to some embodiments of the invention, the malignant disease is a solid tumor or tumor metastasis.

According to some embodiments of the invention, the malignant disease is a hematological malignancy.

According to some embodiments of the invention, the malignant disease is selected from the group consisting of a leukemia, a lymphoma, a myeloma, a melanoma, a sarcoma, a neuroblastoma, a colon cancer, a colorectal cancer, a breast cancer, an ovarian cancer, an esophageal cancer, a synovial cell cancer, a hepatic cancer and a pancreatic cancer.

According to some embodiments of the invention, the subject has a non-malignant disease.

According to some embodiments of the invention, the non-malignant disease is selected from the group consisting of an organ dysfunction or failure, a hematologic disease, a graft related disease, an infectious disease, an autoimmune disease, an inflammation, an allergy, a trauma and an injury.

According to some embodiments of the invention, the infectious disease is a viral disease or a bacterial disease.

According to some embodiments of the invention, the subject is a human subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic illustration of a reduced conditioning T cell depleted bone marrow transplantation (TDBMT) model using veto Tcm cells derived from $CD44^+CD8^+$ memory T cells from OVA immunized mice.

FIGS. 2B-2C are graphs illustrating that $CD8^+CD44^+$ Tcm cells do not induce GvHD in a stringent murine model. Sublethally irradiated (5 Gy) Balb/c (H-2d) mice were transplanted with $5 \times 10^6$ or $10 \times 10^6$ allogeneic OVA-immunized C57BL/6 (H-2b) derived $CD8^+CD44^+$ Tcm cells or fresh $CD8^+CD44^+$ cells. $CD8^+CD44^-$ naïve cells were used as positive control for GvHD. (FIG. 2B) Average weight change during 62 days after transfer of cells. (FIG. 2C) Survival plot depicts the survival time line of the mice in specified groups.

FIG. 2E is a graph illustrating that veto Tcm cells prepared from a population of naturally occurring memory cells ($CD8^+CD44^+$) induce tolerance to TCD alloSCT. Sublethally irradiated (5 Gy) Balb/c ($H-2^d$) mice were transplanted with $20 \times 10^6$ C57BL/6-nude ($H-2^b$) BM cells with or without: $5 \times 10^6$ allogeneic C57BL/6 veto Tcm cells ($H-2^b$) or $5 \times 10^6$ $CD8^+CD44^+$ cells derived from OVA immunized mice or $5 \times 10^6$ allogeneic C57BL/6 freshly isolated $CD8^+CD44^+$ cells. Percentage of donor cells in peripheral blood was analyzed 55 days after transplant by FACS using anti-host ($H-2D^d$) anti-donor ($H-2K^b$) antibodies.

FIGS. 3A-3D are graphs illustrating generation of anti-$3r^d$-party $CD4^-CD56^-$ veto Tcm cells using viral peptides. Human $CD4^-CD56^-$ responders that were established following depletion of $CD4^+$ and $CD56^+$ cells from Donor PBMCs on day 0 were co-cultured against irradiated donor derived DCs pulsed with viral peptides of EBV, CMV and Adenovirus with IL-21 until day +3, with the addition IL-21, IL-15 and IL-7 from day +3-+9. (FIGS. 3A-3B) FACS analysis of veto Tcm phenotype of responder $CD4^-CD56^-$ cells on day 0 (FIG. 3A) and anti-viral Tcm cells generated from them on day 9 of culture (FIG. 3B). (FIGS. 3C-3D) On day +9, cells were harvested and cultured against irradiated host PBMCs for 5 days (i.e. bulk culture) and then harvested and re-stimulated for 7 days against irradiated host PBMCs in limiting dilution analysis (LDA) in the presence of IL-2 for the induction of an effector phenotype. On day +21, $S^{35}$-Methionine LDA killing assay was carried out against ConA-blasts host origin. After a 5 hour mixed lymphocyte reaction (MLR), supernatant was collected from wells and subjected to radioactive count in a β-counter. (FIG. 3C) represents a plot of % responding cultures versus cell number per culture. (FIG. 3D) Represents linear regression plot of % non-responding cultures versus cell number per culture. The frequency (f) of anti-host clones in the specific culture was calculated from the linear regression slope.

FIGS. 5A-5B are graphs illustrating anti viral-veto Tcm cells generated from CD4$^-$CD56$^-$CD45RA$^-$ responders using autologous DCs loaded with viral peptides as third-party stimulation. (FIG. 5A) Phenotype of CD4$^-$CD56$^-$ responders on day 0 and Tcm cells on day +9 (right panel). (FIG. 5B) Phenotype of CD4$^-$CD56$^-$CD45RA$^-$ responders on day 0 and Tcm cells on day +9 (right panel)

FIG. 5C is a graph illustrating limit dilution analysis (LDA) of anti-host CTL precursors frequency in anti-viral Tcm cells generated from CD4$^-$CD56$^-$CD45RA$^-$ and CD4$^-$CD56$^-$ cell fractions, in comparison to fresh CD4$^-$CD56$^-$CD19$^-$ T cells. On day +9 a control population of Fresh CD4$^-$CD56$^-$CD19$^-$ cells was bead-sorted from freshly thawed donor cells. All three donor type cell preparations (i.e. anti-viral veto Tcm CD4$^-$CD56$^-$, anti-viral veto Tcm CD4$^-$CD56$^-$CD45RA$^-$ and fresh CD4$^-$CD56$^-$CD19$^-$ cells) were cultured against irradiated host PBMCs for 5 days on day +9 (i.e. bulk culture) and then harvested and re-stimulated for 7 days against irradiated host PBMCs in LDA in the presence of IL-2 for the induction of an effector phenotype. On day +21, S$^{35}$-Methionine LDA killing assay was carried out against ConA-blasts of host origin. After a 5 hour MLR, supernatant was collected from wells and subjected to radioactive count in a β-counter. A linear regression plot of % non-responding cultures versus cell number per culture is presented. The frequency (f) of anti-host clones in the specific culture was calculated from the linear regression slope.

FIG. 6 is a table summarizing the anti-host T-cell depletion before and after generation of veto Tcm cells directed against viral peptides (as carried out in FIG. 4A and FIGS. 5A-C). Of note, the low anti-host CTL-p frequency and total anti-host CTL-p levels based on the LDA assay (circled on the graph).

FIG. 8 is a table summarizing 10 experiments in which veto Tcm cells were generated from memory T cells by the protocol presented in FIG. 7. Of note, cell recovery and purity was very reproducible.

FIGS. 9A-9H are graphs illustrating a typical FACS analysis of one experiment showing the purity of the veto Tcm cells generated from memory T cells by the protocol presented in FIG. 7. The figures show FACS analysis of each step presented in FIG. 8 as follows: FIGS. 9A-9B illustrate FACS analysis of peripheral blood mononuclear cells (PBMCs) before purification; FIGS. 9C-9D illustrate FACS analysis after CD4$^-$CD56$^-$ purification; FIGS. 9E-F illustrate FACS analysis after CD4$^-$CD56$^-$CD45RA$^-$ purification (i.e. enrichment of CD4-CD56-CD45RO$^+$ cells); FIGS. 9G-9H illustrate FACS analysis of the anti-viral Tcm cells.

DESCRIPTION OF SPECIFIC EMBODIMENTS
OF THE INVENTION

The present invention, in some embodiments thereof, relates to veto cells generated from memory T cells and, more particularly, but not exclusively, to methods of their manufacture and to the use of same in transplantation and in disease treatment.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Bone marrow (BM) transplantation offers a curative treatment for many patients with hematological malignancies and other disorders (e.g. hematological diseases, organ failure). Furthermore, BM can be co-transplanted with various other organs (e.g. kidney or liver graft from the same organ donor) in order to increase success of transplantation by induction of chimerism. However, the BM graft contains donor T cells which respond to the host antigens (Ags) and cause multi-system graft-versus-host disease (GvHD). The problem of GvHD, which is almost uniformly lethal in such settings, can be prevented by transplantation of T cell depleted bone marrow (TDBMT). However, the benefit of GvHD prevention may be offset by a markedly increased rate of graft rejection.

One approach to overcome rejection of allogeneic TDBMT made use of various veto cell preparations as taught by PCT Publication Nos. WO 2001/49243, WO 2007/023491, WO 2010/049935, WO 2012/032526 and WO 2013/035099. However, graft rejection and GvHD are still of major concern in adoptive cell therapy, especially in allogeneic settings.

While reducing the present invention to practice, the present inventors have uncovered an improved population of veto cells which also comprise an anti-disease activity (e.g. anti-viral activity) without inducing a graft versus host (GvH) reaction. These novel cells are generated by depleting alloreactive clones from memory T cells by way of antigen activation.

Figure 2A:
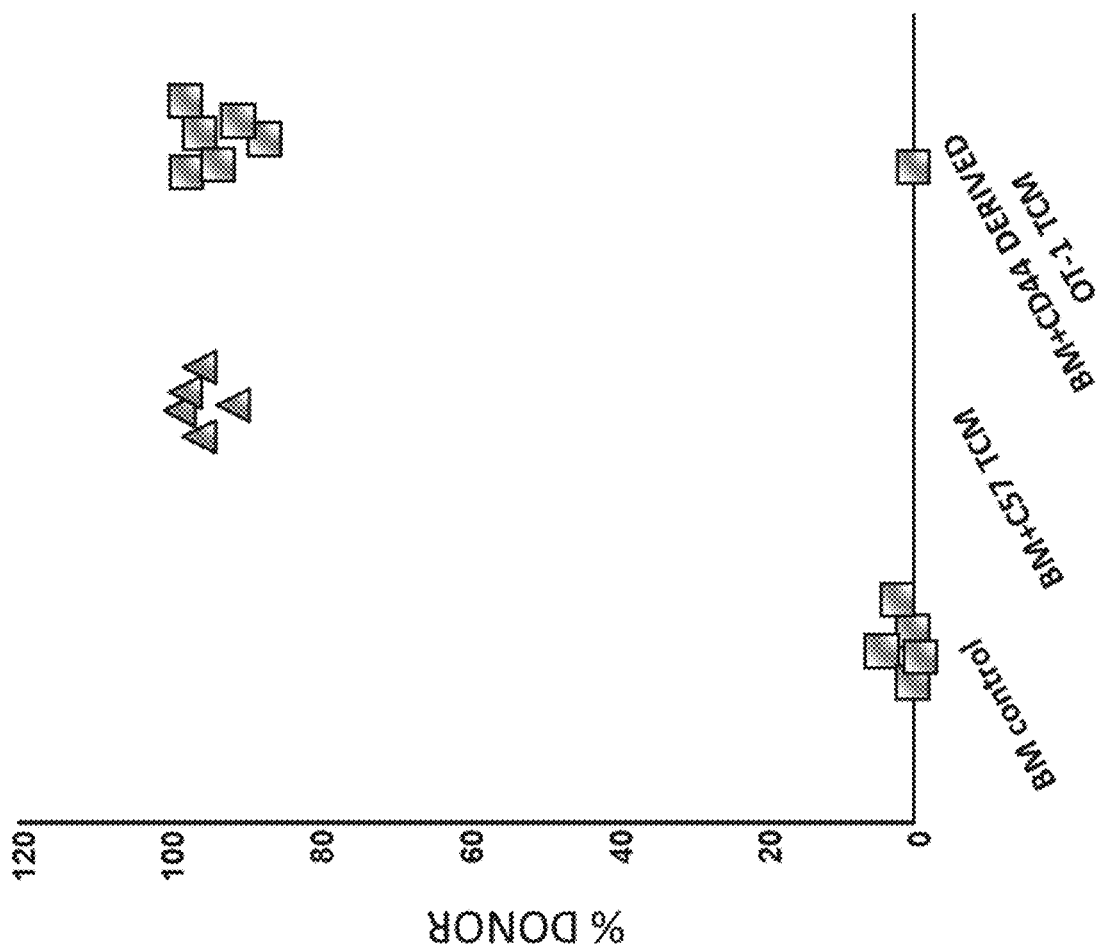
FIG. 2A is a graph illustrating that veto Tcm cells prepared from the entire population of antigen experienced cells ($CD8^+CD44^+$) after immunization of OT1 mice with ovalbumin induce tolerance to T cell depleted (TCD) allogeneic stem cell transplant (SCT). Sublethally irradiated (5.25 Gy) Balb/c ($H-2^d$) mice were transplanted with $20 \times 10^6$ C57BL/6-nude ($H-2^b$) BM cells with or without: $5 \times 10^6$ allogeneic C57BL/6 veto Tcm cells ($H-2^b$) or $5 \times 10^6$ $CD8^+CD44^+$ cells derived from OT-1 OVA immunized mice. Percentage of donor cells in peripheral blood was analyzed 45 days after transplant by FACS using anti-host ($H-2D^d$) anti-donor ($H-2K^b$) antibodies.
Figure 2C:
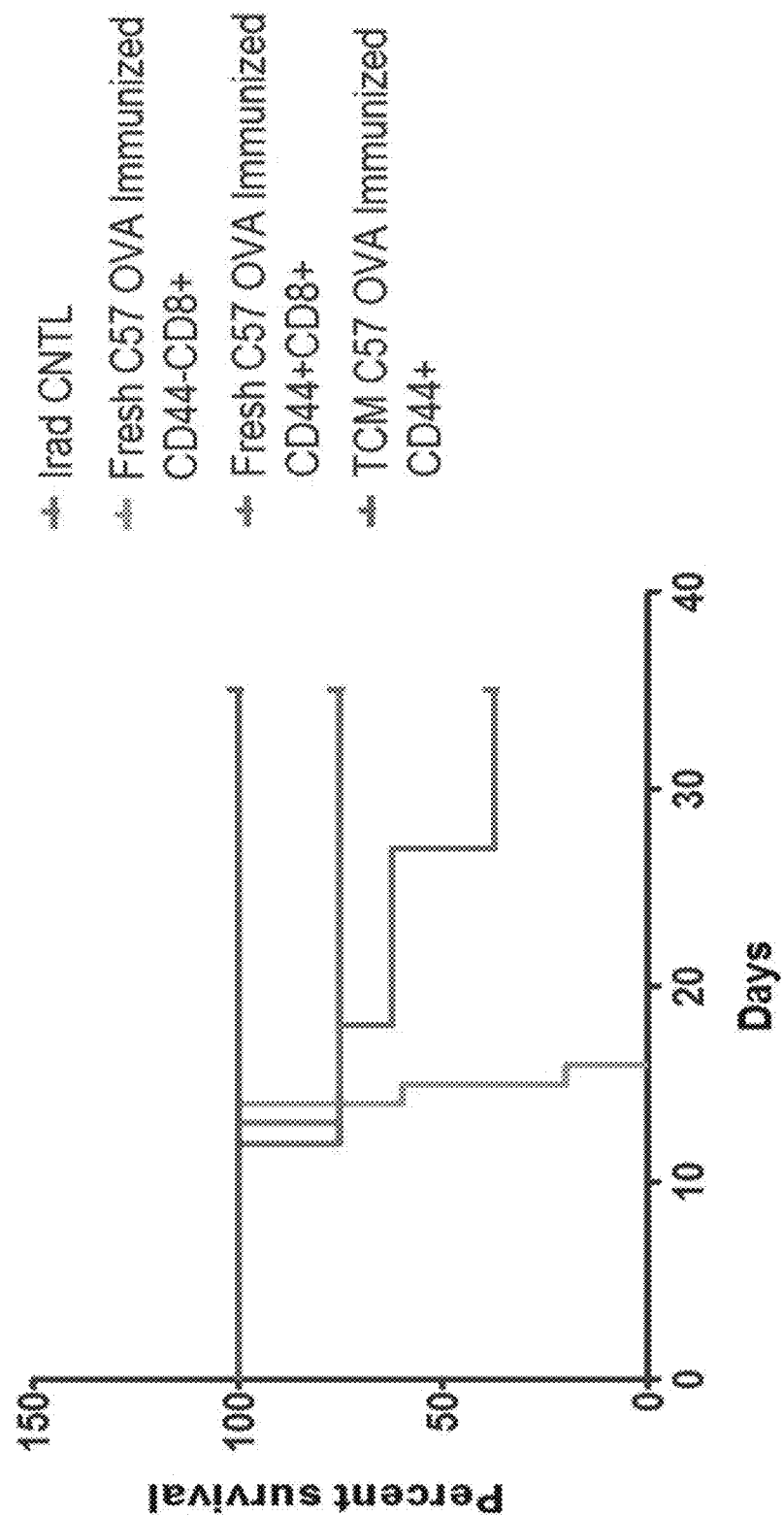

As is shown herein below and in the Examples section which follows, the present inventors have provided new methods of generating veto cells for HLA mismatched (e.g. allogeneic) applications starting from memory T cells. Specifically, as shown in FIG. 1, the present inventors utilized a mouse model for generation of veto Tcm cells from naturally occurring memory T cells. The Tcm cells generated from memory T cells induced tolerance in a reduced conditioning T cell depleted bone marrow transplantation (TDBMT) model, without a graft versus host reactivity (FIG. 2A), and exhibited marked enhancement of chimerism following a reduced intensity conditioning protocol (FIG. 2E). However, it was shown that fresh CD8$^+$CD44$^+$ memory cells (which did not undergo antigen activation) induced significant lethality and weight loss due to GvHD (FIGS. 2B-2C).

Figure 3B:
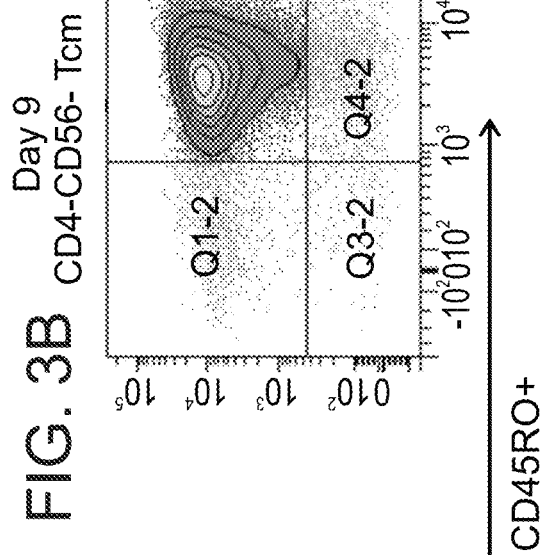
Figure 3A:
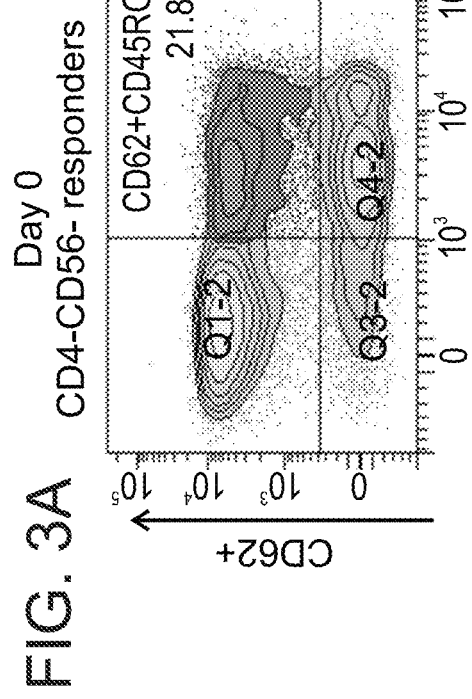
Figure 3C:
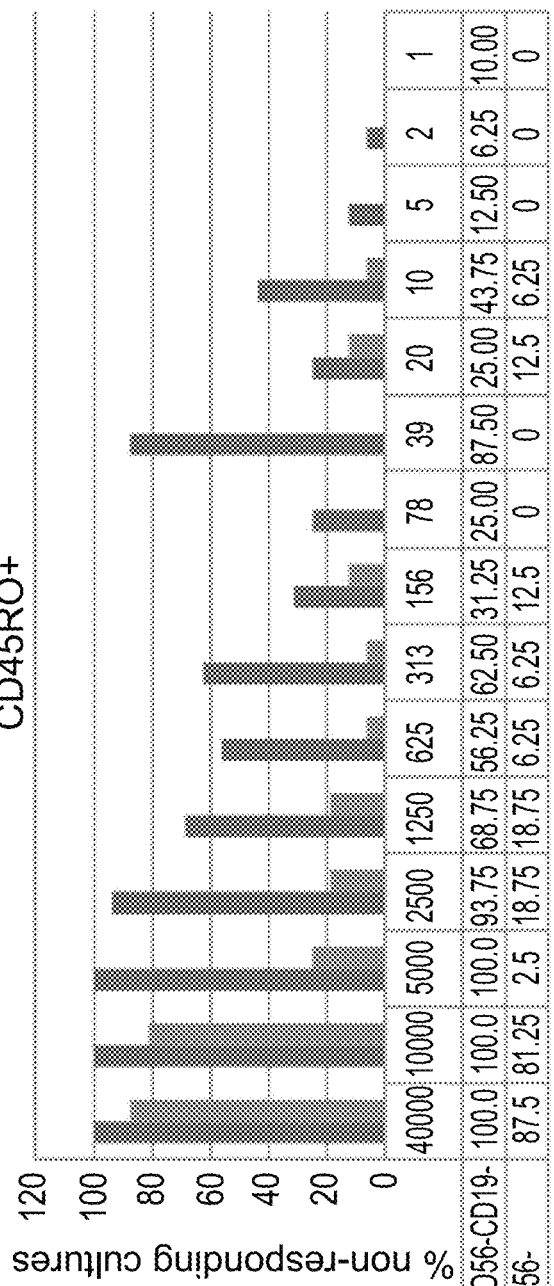
Figure 4A:
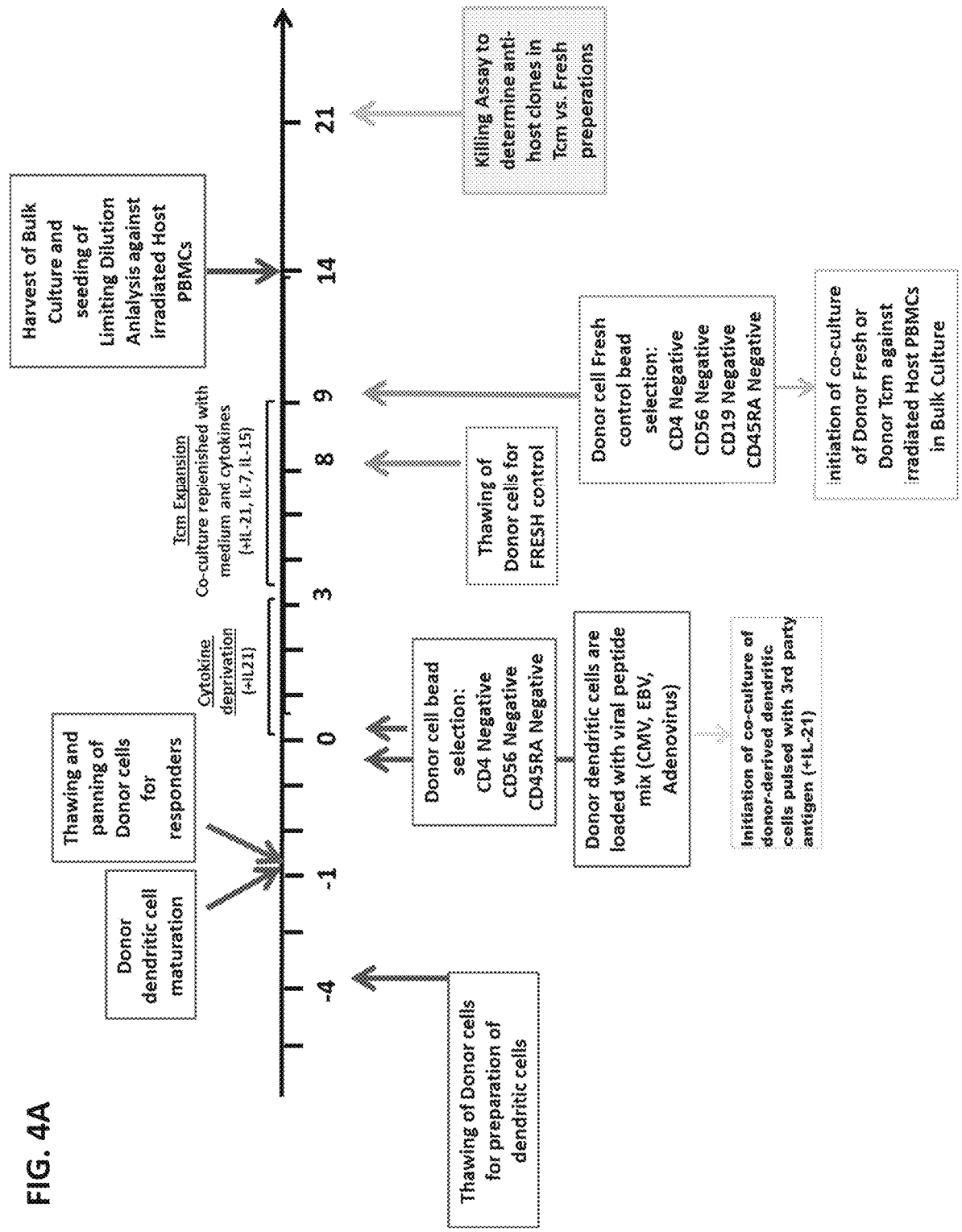
FIG. 4A is a schematic representation of the protocol for generation of leukapheresis derived anti-viral CD4-CD56-CD45RA– human veto Tcm cells and testing of their anti-host reactivity.

Next, viral antigens were used to generate human Tcm veto cells from a CD4-CD56-cell population. As illustrated in FIGS. 3A-3B, cells cultured in the presence of viral antigens, presented on autologous dendritic cells, comprised 93% Tcm phenotype (CD62$^+$CD45RO$^+$ cells) 9 days from the beginning of culture. Furthermore, these Tcm cells afforded a two-log depletion of host-alloreactive clones as compared to fresh CD4$^-$CD56$^-$ cells (FIGS. 3C-3D and Table 2, below). Veto cells were then generated from human memory cells by first depleting peripheral blood mononuclear cells (PBMC), obtained from a cell donor, of $CD4^+$, $CD56^+$ and $CD45RA^+$ cells (FIG. 4A). Accordingly, the remaining population of cells comprised donor memory CD8+ T cells. The memory CD8+ T cells were co-cultured with dendritic cells (of the same cell donor), wherein the dendritic cells have been manipulated to express an antigen (e.g. viral antigen cocktail including EBV, CMV and Adenovirus). For the first 3 days, the cell culture was supplemented with IL-21, and then from day 3, IL-21, IL-15 and IL-7 were added to the culture until day 9. The resulting population of cells comprised a Tcm phenotype and did not exert any anti-host reactivity (as illustrated in FIGS. 5A-5C and 6).

Taken together, depletion of alloreactive clones in a T cell memory pool by way of antigen activation (e.g. using viral antigens, tumor antigens) may solve the problem of residual GvHD remaining in the memory T cell pool. Furthermore, these results suggest that the novel preparation of veto cells generated from memory cells can be used in cell therapy for the induction of transplantation tolerance, free of GvHD complications, as well as for disease treatment (e.g. for anti-viral or anti-cancer applications).

Thus, according to one aspect of the present invention there is provided a method of generating an isolated population of non graft versus host disease (GvHD) inducing cells comprising a central memory T-lymphocyte (Tcm) phenotype, the cells being tolerance inducing cells and/or endowed with anti-disease activity, and capable of homing to the lymph nodes following transplantation, the method comprising: (a) providing a population of at least 70% memory T cells; (b) contacting the population of memory T cells with an antigen or antigens so as to allow enrichment of antigen reactive cells; and (c) culturing the cells resulting from step (b) in the presence of cytokines so as to allow proliferation of cells comprising the central memory T-lymphocyte (Tcm) phenotype, thereby generating the isolated population of non-GVHD inducing cells.

The phrase "isolated population of cells" as used herein refers to cells which have been isolated from their natural environment (e.g., the human body).

The term "non graft versus host disease" or "non-GvHD" as used herein refers to having substantially reduced or no graft versus host (GvH) inducing reactivity. Thus, the cells of the present invention are generated as to not significantly cause graft versus host disease (GvHD) as evidenced by survival, weight and overall appearance of the transplanted subject 30-120 days following transplantation. Methods of evaluating a subject for reduced GvHD are well known to one of skill in the art.

According to one embodiment, the cells of the present invention have at least 10%, at least 20%, at least 30%, at least 40%, at least 50%, at least 55%, at least 60%, at least 65%, at least 70%, at least 75%, at least 80%, at least 85%, at least 90%, at least 95% or even 100% reduced reactivity against a host relative to cells not generated according to the present teachings.

The phrase "central memory T-lymphocyte (Tcm) phenotype" as used herein refers to a subset of T cytotoxic cells which home to the lymph nodes. Cells having the Tcm phenotype, in humans, typically comprise a CD3+/CD8+/CD62L+/CD45RO+/CD45RA− signature. It will be appreciated that Tcm cells may express all of the signature markers on a single cell or may express only part of the signature markers on a single cell. Determination of a cell phenotype can be carried out using any method known to one of skill in the art, such as for example, by Fluorescence-activated cell sorting (FACS) or capture ELISA labeling.

According to one embodiment, at least 20%, at least 30%, at least 40%, at least 50%, at least 55%, at least 60%, at least 65%, at least 70%, at least 75%, at least 80%, at least 85%, at least 90%, at least 95% or even 100% of the isolated population of cells have the Tcm cell signature.

According to a specific embodiment, about 20-40%, about 30-50%, about 40-60%, about 50-70%, about 60-80%, about 70-90%, about 80-100%, or about 90-100% of the isolated population of cells have the Tcm cell signature.

The isolated population of non-GvHD inducing cells of the invention is also referred to herein as "Tcm cells".

As mentioned, Tcm cells typically home to the lymph nodes following transplantation. According to some embodiments, the isolated population of cells of the present invention may home to any of the lymph nodes following transplantation, as for example, the peripheral lymph nodes and mesenteric lymph nodes. The homing nature of these cells allows them to exert their veto effect in a rapid and efficient manner.

The isolated population of Tcm cells of the present invention are tolerance-inducing cells.

The phrase "tolerance inducing cells" as used herein refers to cells which provoke decreased responsiveness of the recipient's cells (e.g. recipient's T cells) when they come in contact with the recipient's cells as compared to the responsiveness of the recipient's cells in the absence of administered tolerance inducing cells. Tolerance inducing cells include veto cells (i.e. T cells which lead to apoptosis of host T cells upon contact with same) as was previously described in PCT Publication Nos. WO 2001/049243 and WO 2002/102971.

The term "veto activity" relates to immune cells (e.g. donor derived T cells) which lead to inactivation of anti-donor recipient T cells upon recognition and binding to the veto cells. According to one embodiment, the inactivation results in apoptosis of the anti-donor recipient T cells.

Additionally or alternatively, the isolated population of Tcm cells of the present invention comprise anti-disease activity.

The term "anti-disease activity" refers to the function of the Tcm cells against a diseased cell. The anti-disease activity may be directly against a diseased cell, e.g. killing capability of the diseased cell. This activity may be due to TCR independent killing mediated by LFA1-I/CAM1 binding [Arditti et al., Blood (2005) 105(8):3365-71. Epub 2004 Jul. 6]. Additionally or alternatively, the anti-disease activity may be indirect, e.g. by activation of other types of cells (e.g. CD4+ T cells, B cells, monocytes, macrophages, NK cells) which leads to death of the diseased cell (e.g. by killing, apoptosis, or by secretion of other factors, e.g. antibodies, cytokines, etc.).

A diseased cell may comprise, for example, a virally infected cell, a bacterial infected cell, a cancer cell [e.g. cell of a solid tumor or leukemia/lymphoma cell, also referred to herein as graft versus leukemia (GVL) activity of the Tcm cells], a cell associated with an autoimmune disease, a cell associated with an allergic response, or a cell altered due to stress, radiation or age.

According to some embodiments, the Tcm cells of the present invention may be non-genetically modified cells or genetically modified cells (e.g. cells which have been genetically engineered to express or not express specific genes, markers or peptides or to secrete or not secrete specific cytokines). Any method known in the art may be implemented in genetically engineering the cells, such as by inactivation of the relevant gene/s or by insertion of an antisense RNA interfering with polypeptide expression (see e.g. WO/2000/039294, which is hereby incorporated by reference).

According to some embodiments of the invention there is provided a method of generating the isolated population of cells, the method comprising (a) providing a population of memory T cells; (b) contacting the population of memory T cells with an antigen or antigens so as to allow enrichment of antigen reactive cells; and (c) culturing the cells resulting from step (b) in the presence of cytokines so as to allow proliferation of cells comprising the central memory T-lymphocyte (Tcm) phenotype.

The term "memory T cells" as used herein refers to a subset of T lymphocytes which have previously encountered and responded to an antigen, also referred to as antigen experienced T cells.

According to one embodiment, the memory T cells comprise at least about 50%, at least about 60%, at least about 70%, at least about 80%, at least about 90%, at least about 95%, at least about 99%, or even 100% of the population of cells.

According to one embodiment, the memory T cells comprise cytotoxic T cells expressing a CD8 marker (i.e. $CD8^+$ T cells).

According to another embodiment, the memory T cells comprise a $CD8^+CD45RO^+$ phenotype.

According to another embodiment, the memory T cells comprise a $CD8^+CD45RA^-$ phenotype.

According to another embodiment, the memory T cells comprise a $CD8^+CD45RO^+CD45RA^-$ phenotype.

Selection of memory $CD8^+$ T cells may be effected by selection of cells co-expressing $CD8^+$ and $CD45RA^-$ and/or cells co-expressing $CD8^+$ and $CD45RO^+$ and may be carried out using any method known in the art, such as by affinity based purification (e.g. such as by the use of MACS beads, FACS sorter and/or capture ELISA labeling).

Selection of memory $CD8^+$ T cells may be further effected by selection of effector T cells and central memory T cells, the latter expressing e.g. CD62L, CCR7, CD27 and/or CD28.

According to one embodiment, memory T cells are obtained from peripheral blood mononuclear cells (PBMCs).

According to one embodiment, memory T cells are obtained from a lymphoid tissue, such as from lymph nodes or spleen.

In order to obtain a cell population comprising a high purity of memory T cells (e.g. at least about 50-70% memory T cells) or in order to increase the number of memory T cells, PBMCs may be depleted of naïve cells, e.g. $CD45RA^+$ cells, of adherent cells (e.g. monocytes, macrophages), of $CD4^+$ cells (e.g. T helper cells), of $CD56^+$ cells (e.g. NK cells) or any other cells not comprising a memory T cell phenotype.

Depletion of naïve T cells (e.g. expressing $CD45RA^+$ cells), $CD4^+$ and/or $CD56^+$ cells may be carried out using any method known in the art, such as by affinity based purification (e.g. such as by the use of MACS beads, FACS sorter and/or capture ELISA labeling).

Depletion of adherent cells may be carried out using any method known in the art, e.g. by culturing the PBMCs on a cell culture dish (e.g. for 2-6 hours) and collecting the non-adherent cells.

According to one embodiment, the memory T cells are devoid of $CD45RA^+$ cells.

According to one embodiment, the memory T cells are devoid of $CD4^+$ and/or $CD56^+$ cells.

In order to deplete alloreactive clones from the memory T cell pool, the memory T cells are contacted with an antigen or antigens.

As used herein the phrase "antigen or antigens" refers to a soluble or non-soluble (such as membrane associated) molecule capable of inducing an immune response.

For example, an antigen or antigens can be whole cells (e.g. live or dead cells), cell fractions (e.g. lysed cells), cell antigens (e.g. cell surface antigens), a protein extract, a purified protein or a synthetic peptide. For example, an antigen or antigens of some embodiment of the invention include antigens associated with a malignant disease (e.g. tumor antigens), antigens associated with an autoimmune disease (i.e. autoimmune antigens), antigens associated with an allergic reaction (i.e. allergic antigens), antigens of viruses (i.e. viral antigens), antigens of bacteria (i.e. bacterial antigens) or antigens of fungi (e.g. fungi antigens).

According to an embodiment, the antigen or antigens is of an infectious organism (e.g., viral, bacterial, fungal organism) which typically affects immune comprised subjects, such as transplantation patients. Exemplary infectious organisms which may affect immune comprised patients include, but are not limited to, viruses such as parvovirus (e.g. parvovirus B19), rotavirus, varicella-zoster virus (VZV), Herpes simplex virus (HSV), cytomegalovirus (CMV), Epstein-Barr virus (EBV), Polyomavirus (e.g. BK virus); bacteria such as *S. pneumoniae, P. aeruginosa, Legionella pneumophila, L. monocytogenes, Nocardia species, Mycobacterium species, S. aureus, Nocardia species, P. aeruginosa, Serratia* species, *Chromobacterium*, streptococci, *Burkholderia, Mycobacterium* (e.g. *Mycobacterium avium-intracellulare* complex), encapsulated bacteria such as *S. pneumoniae, H. influenzae* and *N. meningitidis*; fungi such as *P. jiroveci, Candida*, and *Aspergillus*; and parasites such as *Toxoplasma* species, cryptosporidia and *Strongyloides* species.

According to one embodiment, the antigen is a viral antigen, such as but not limited to, an antigen of Epstein-Barr virus (EBV), Adenovirus (Adv), cytomegalovirus (CMV), cold viruses, flu viruses, hepatitis A, B, and C viruses, herpes simplex, HIV, influenza, Japanese encephalitis, measles, polio, rabies, respiratory syncytial, rubella, smallpox, varicella zoster, rotavirus, West Nile virus, Polyomavirus (e.g. BK virus) or zika virus.

As further particular examples of viral antigens, Adenovirus antigens include, but are not limited tom Adv-penton or Adv-hexon; CMV antigens include, but are not limited to, envelope glycoprotein B, CMV IE-1 and CMV pp65; EBV antigens include, but are not limited to, EBV LMP2, EBV BZLF1, EBV EBNA1, EBV P18, and EBV P23; hepatitis antigens include, but are not limited to, the S, M, and L proteins of hepatitis B virus, the pre-S antigen of hepatitis B virus, HBCAG DELTA, HBV HBE, hepatitis C viral RNA, HCV NS3 and HCV NS4; herpes simplex viral antigens include, but are not limited to, immediate early proteins and glycoprotein D; HIV antigens include, but are not limited to, gene products of the gag, pol, and env genes such as HIV gp32, HIV gp41, HIV gp120, HIV gp160, HIV P17/24, HIV P24, HIV P55 GAG, HIV P66 POL, HIV TAT, HIV GP36, the Nef protein and reverse transcriptase; influenza antigens include, but are not limited to, hemagglutinin and neuraminidase; Japanese encephalitis viral antigens include, but are not limited to, proteins E, M-E, M-E-NS1, NS1, NS1-NS2A and 80% E; measles antigens include, but are not limited to, the measles virus fusion protein; rabies antigens include, but are not limited to, rabies glycoprotein and rabies nucleoprotein; respiratory syncytial viral antigens include, but are not limited to, the RSV fusion protein and the M2 protein; rotaviral antigens include, but are not limited to, VP7sc; rubella antigens include, but are not limited to, proteins E1 and E2; and varicella zoster viral antigens include, but are not limited to, gpI and gpII.

According to one embodiment, the antigen is a bacterial antigen, such as but not limited to, an antigen of anthrax; gram-negative bacilli, chlamydia, diptheria, haemophilus influenza, *Helicobacter pylori*, malaria, *Mycobacterium tuberculosis*, pertussis toxin, pneumococcus, rickettsiae, *staphylococcus, streptococcus* and tetanus.

As further particular examples of bacterial antigens, anthrax antigens include, but are not limited to, anthrax protective antigen; gram-negative bacilli antigens include, but are not limited to, lipopolysaccharides; haemophilus influenza antigens include, but are not limited to, capsular polysaccharides; diptheria antigens include, but are not limited to, diptheria toxin; *Mycobacterium tuberculosis* antigens include, but are not limited to, mycolic acid, heat shock protein 65 (HSP65), the 30 kDa major secreted protein and antigen 85A; pertussis toxin antigens include, but are not limited to, hemagglutinin, pertactin, FIM2, FIM3 and adenylate cyclase; pneumococcal antigens include, but are not limited to, pneumolysin and pneumococcal capsular polysaccharides; rickettsiae antigens include, but are not limited to, rompA; streptococcal antigens include, but are not limited to, M proteins; and tetanus antigens include, but are not limited to, tetanus toxin.

According to one embodiment, the antigen is a superbug antigen (e.g. multi-drug resistant bacteria). Examples of superbugs include, but are not limited to, *Enterococcus faecium, Clostridium difficile, Acinetobacter baumannii, Pseudomonas aeruginosa*, and Enterobacteriaceae (including *Escherichia coli, Klebsiella pneumoniae, Enterobacter* spp.).

According to one embodiment, the antigen is a fungal antigen. Examples of fungi include, but are not limited to, *candida*, coccidiodes, *cryptococcus, histoplasma, leishmania, plasmodium*, protozoa, parasites, schistosomae, tinea, *toxoplasma*, and *Trypanosoma cruzi*.

As further particular examples of fungal antigens, coccidiodes antigens include, but are not limited to, spherule antigens; cryptococcal antigens include, but are not limited to, capsular polysaccharides; *histoplasma* antigens include, but are not limited to, heat shock protein 60 (HSP60); *leishmania* antigens include, but are not limited to, gp63 and lipophosphoglycan; *Plasmodium falciparum* antigens include, but are not limited to, merozoite surface antigens, sporozoite surface antigens, circumsporozoite antigens, gametocyte/gamete surface antigens, protozoal and other parasitic antigens including the blood-stage antigen pf 155/RESA; schistosomae antigens include, but are not limited to, glutathione-S-transferase and paramyosin; tinea fungal antigens include, but are not limited to, trichophytin; *toxoplasma* antigens include, but are not limited to, SAG-1 and p30; and *Trypanosoma cruzi* antigens include, but are not limited to, the 75-77 kDa antigen and the 56 kDa antigen.

According to one embodiment, the antigen is an antigen expressed by cells associated with unwanted autoimmune or allergic condition. Exemplary autoimmune conditions include, but are not limited to, acute necrotizing hemorrhagic encephalopathy, allergic asthma, alopecia areata, anemia, aphthous ulcer, arthritis (including rheumatoid arthritis, juvenile rheumatoid arthritis, osteoarthritis, psoriatic arthritis), asthma, autoimmune thyroiditis, conjunctivitis, Crohn's disease, cutaneous lupus erythematosus, dermatitis (including atopic dermatitis and eczematous dermatitis), diabetes, diabetes mellitus, erythema nodosum leprosum, keratoconjunctivitis, multiple sclerosis, myasthenia gravis, psoriasis, scleroderma, Sjogren's syndrome, including keratoconjunctivitis sicca secondary to Sjogren's syndrome, Stevens-Johnson syndrome, systemic lupus erythematosis, ulcerative colitis, vaginitis and Wegener's granulomatosis.

Examples of autoimmune antigens include, but are not limited to, glutamic acid decarboxylase 65 (GAD 65), native DNA, myelin basic protein, myelin proteolipid protein, acetylcholine receptor components, thyroglobulin, and the thyroid stimulating hormone (TSH) receptor.

Examples of allergic antigens include, but are not limited to, pollen antigens such as Japanese cedar pollen antigens, ragweed pollen antigens, rye grass pollen antigens, animal derived antigens (such as dust mite antigens and feline antigens), histocompatibility antigens, and penicillin and other therapeutic drugs.

According to one embodiment, the antigen is an antigen (or part thereof, e.g. antigen epitope) expressed by tumor cells. According to one embodiment, the antigen (or part thereof) is derived from a protein expressed in a hematopoietic tissue (e.g. hematopoietic malignancy such as leukemia antigen) or expressed in a solid tumor (e.g. melanoma, pancreatic cancer, liver cancer, gastrointestinal cancer, etc.).

Examples of tumor antigens include, but are not limited to, A33, BAGE, Bcl-2, B cell maturation antigen (BCMA), BCR-ABL, β-catenin, cancer testis antigens (CTA e.g. MAGE-1, MAGE-A2/A3 and NY-ESO-1), CA 125, CA 19-9, CA 50, CA 27.29 (BR 27.29), CA 15-3, CD5, CD19, CD20, CD21, CD22, CD33, CD37, CD45, CD123, CEA, c-Met, CS-1, cyclin B1, DAGE, EBNA, EGFR, ELA2, ephrinB2, estrogen receptor, FAP, ferritin, folate-binding protein, GAGE, G250/CA IX, GD-2, GM2, gp75, gp100 (Pmel 17), HA-1, HA-2, HER-2/neu, HM1.24, HPV E6, HPV E7, hTERT, Ki-67, LRP, mesothelin, mucin-like cancer-associated antigen (MCA), MUC1, p53, PR1, PRAME, PRTN3, RHAMM (CD168), WT-1. Further tumor antigens are provided in Molldrem *J. Biology of Blood and Marrow Transplantation* (2006) 12:13-18; Alatrash G. and Molldrem J., *Expert Rev Hematol*. (2011) 4(1): 37-50; Renkvist et al., *Cancer Immunol Immunother* (2001) 50:3-15; van der Bruggen P, Stroobant V, Vigneron N, Van den Eynde B. Peptide database: T cell-defined tumor antigens. *Cancer Immun* (2013), www(dot)cancerimmunity(dot)org/peptide/; Rittenhouse, Manderino, and Hass, *Laboratory Medicine* (1985) 16(9) 556-560; all of which are incorporated herein by reference.

Following is a list of tumor antigens which may be used according to the teachings of some embodiments of the invention.

TABLE 1

| | list of tumor antigens | | |
|---|---|---|---|
| Cancer | TAA/Marker | GenBank Accession No. of the tumor antigens | HLA |
| Transitional cell carcinoma | Uroplakin II (UPKII) | NP_006751.1 | HLA-A2 |
| Transitional cell carcinoma | Uroplakin Ia (UPK1A) | NP_001268372.1; NP_008931.1 | HLA-A2 |
| Carcinoma of the prostate | prostate specific antigen (NPSA) | AAO16090.1 | HLA-A2 |
| Carcinoma of the prostate | prostate specific membrane antigen (PSCA) | NP_005663.2 | HLA-A2 |
| Carcinoma of the prostate | prostate acid phosphatase (ACPP) | NP_001090.2; NP_001127666.1; NP_001278966.1 | HLA-A2 |
| Breast cancer | BA-46 MFGE8 milk fat globule-EGF factor 8 protein [lactadherin] | NP_001108086.1; NP_005919.2; | HLA-A2 |
| Breast cancer | Mucin 1 (MUC1) | NP_001018016.1; NP_001018017.1; NP_001037855.1; NP_001037856.1; NP_001037857.1; NP_001037858.1; NP_001191214.1; NP_001191215.1; NP_001191216.1; NP_001191217.1; NP_001191218.1; NP_001191219.1; NP_001191220.1; NP_001191221.1; NP_001191222.1; NP_001191223.1; NP_001191224.1; NP_001191225.1; NP_001191226.1; NP_002447.4 | HLA-A2 |
| Melanoma | premelanosome protein (PMEL; also known as Gp100) | NP_001186982.1; NP_001186983.1; NP_008859.1 | HLA-A2 |
| Melanoma | melan-A (MLANA; also known as MART1) | NP_005502.1; | HLA-A2 |
| All tumors | telomerase reverse transcriptase (TERT) | NP_001180305.1; NP_937983.2 | HLA-A2 |
| Leukemia and Burkitts Lymphoma | TAX tax p40 [Human T-lymphotropic virus 1] and Tax [Human T-lymphotropic virus 4]; | NP_057864.1; YP_002455788.1 | HLA-A2 |
| Carcinomas | NY-ESO cancer/testis antigen IB (CTAG1B) | NP_001318.1 | HLA-A2 |
| Melanoma | Melanoma antigen family Al (MAGEA1) | NP_004979.3 | HLA-A2 |
| Melanoma | Melanoma antigen family A3 (MAGEA3, MAGE-A3) | NP_005353.1 | HLA-A24 |
| Carcinomas | HER2; erb-b2 receptor tyrosine kinase 2 (ERBB2) | NP_001005862.1; NP_001276865.1; NP_001276866.1; NP_001276867.1; NP_004439.2; | HLA-A2 |
| Melanoma | Beta-catenine; catenin (cadherin-associated protein), beta 1, 88 kDa (CTNNB1) | NP_001091679.1; NP_001091680.1; NP_001895.1; | HLA-A24 |
| Melanoma | Tyrosinase (TYR) | NP_000363.1 | HLA-DRB1 |
| Leukemia | Bcr-abl | AAA35594.1 | HLA-A2 |
| Head and neck | caspase 8, apoptosis-related cysteine peptidase (CASP8) | NP_001073593.1; NP_001073594.1; NP_001219.2; NP_203519.1; NP_203520.1; NP_203522.1 | HLA-B35 |

According to one embodiment, the antigen comprises one antigen (e.g. viral, bacterial or tumor antigen).

According to one embodiment, the antigen or antigens comprise two or more antigens (e.g. a mixture of antigens of one group of antigens, e.g. viral antigens, tumor antigens, etc.; or a mixture of antigens from different groups of antigens, e.g. viral and bacterial antigens, viral and tumor antigens, viral and autoimmune antigens, tumor and autoimmune antigens, or autoimmune and allergic antigens).

According to one embodiment, the antigen or antigens comprise two, three, four, five or more antigens (e.g. in a single formulation or in several formulations).

According to one embodiment, the antigen or antigens comprise two, three, four, five or more tumor antigens (e.g. in a single formulation or in several formulations).

According to one embodiment, the antigen or antigens comprise two, three, four, five or more viral antigens (e.g. in a single formulation or in several formulations).

According to a particular embodiment, the antigen or antigens comprise three viral antigens, e.g. EBV peptide, CMV peptide and Adv peptide.

According to a particular embodiment, the antigen or antigens comprise two or more of EBV-LMP2, EBV-BZLF1, EBV-EBNA1, CMV-pp65, CMV-IE-1, Adv-penton and Adv-hexon (e.g. two, three, four, five, six or all seven antigens).

According to a particular embodiment, the antigen or antigens comprise a mixture of pepmixes which are overlapping peptide libraries (e.g. 15mers overlapping by 11 amino acids) spanning the entire protein sequence of three viruses: CMV, EBV, and Adeno (such pepmixes can be commercially bought e.g. from JPT Technologies, Berlin, Germany).

According to another particular embodiment, the antigen or antigens comprise a mixture of seven pepmixes spanning EBV-LMP2, EBV-BZLF1, EBV-EBNA1, CMV-pp65, CMV-IE-1, Adv-penton and Adv-hexon at a concentration of e.g. 100 ng/peptide or 700 ng/mixture of the seven peptides.

According to a particular embodiment, the viral antigens further comprise a bacterial antigen or antigens.

In order to stimulate an immune response of the memory T cells, additional stimulatory antigens may be used such as, but not limited to, ovalbumin, DNP (dinitrophenyl), KLH (keyhole limpet hemocyanin).

According to one embodiment, the antigen or antigens is a "third party antigen or antigens" i.e. a soluble or non-soluble (such as membrane associated) antigen or antigens which are not present in either the donor or recipient. For example, a third party antigen can be a third party cell.

Third party cells can be either allogeneic or xenogeneic with respects to the donor and recipient (explained in further detail hereinbelow). In the case of allogeneic third party cells, such cells have HLA antigens different from that of the donor but which are not cross reactive with the recipient HLA antigens, such that anti-third party cells generated against such cells are not reactive against a transplant or recipient antigens.

According to an embodiment of the present invention the allogeneic or xenogeneic third party cells are stimulatory cells selected from the group consisting of cells purified from peripheral blood lymphocytes (PBL), spleen or lymph nodes, cytokine-mobilized PBLs, in vitro expanded antigen-presenting cells (APC), in vitro expanded dendritic cells (DC) and artificial antigen presenting cells.

Antigens of the invention can be presented on the cellular, viral, fungal or bacterial surfaces or derived and/or purified therefrom. Additionally, a viral, fungal or bacterial antigen can be displayed on an infected cell or a cellular antigen can be displayed on an artificial vehicle (e.g. liposome) or on an artificial antigen presenting cell (e.g. cell line transfected with the antigen or antigens). Thus, viral, bacterial or fungal antigens can be presented by cells infected therewith or otherwise made to express viral/bacterial/fungi peptides. Similarly, tumor antigens, autoimmune antigens or allergic antigens can be presented by cells made to express these proteins.

Utilizing cells, virally infected cells, bacteria infected cells, viral peptides presenting cells or bacteria peptides presenting cells as antigens is particularly advantageous since such antigens include a diverse array of antigenic determinants and as such direct the formation of Tcm cells of a diverse population, which may further serve in faster reconstitution of T cells in cases where such reconstitution is required, e.g., following lethal or sublethal irradiation or chemotherapy procedure (as discussed in detail below) or to combat diseases (as discussed in detail below).

Thus, antigen presenting cells (autologous or non-autologous, as discussed below), cell lines, artificial vehicles (such as a liposome) or artificial antigen presenting cells (e.g. leukemic or fibroblast cell line transfected with the antigen or antigens), can be used to present short synthetic peptides fused or loaded thereto or to present protein extracts or purified proteins. Such short peptides, protein extracts or purified proteins may be viral-, bacterial-, fungal-, tumor-, autoimmune- or allergic-antigen derived peptides or peptides representing any other antigen.

Dedicated software can be used to analyze viral, bacterial, fungal, tumor, autoimmune or allergic antigen sequences to identify immunogenic short peptides, i.e., peptides presentable in context of major histocompatibility complex (MHC) class I or MHC class II.

Furthermore, the artificial vehicles or artificial APC of the present invention may be engineered to exhibit MHC without being pulsed with an exogenous peptide. Thus, according to one embodiment, the artificial APC comprises K562 tumor cells transfected with a MHC determinant (e.g. autologous with respect to the memory T cell) and a co-stimulatory molecule [as previously described e.g. Suhoski M M et al., Mol Ther. (2007) 15(5): 981-8], or fibroblasts transfected with same.

According to one embodiment, the antigen or antigens are presented by antigen presenting cells (e.g. DCs) autologous with respect to the memory T cells, e.g. of the same origin (e.g. of the same donor), in order to enable memory T cell recognition in the context of MHC class I or MHC class II.

According to one embodiment, the antigen or antigens are presented by genetically modified antigen presenting cells or artificial antigen presenting cells exhibiting MHC antigens (also referred to as human leukocyte antigen (HLA)) recognizable by the memory T cells.

According to one embodiment, the antigen presenting cells comprise human cells.

According to one embodiment, the antigen presenting cells comprise dendritic cells (DCs).

According to one embodiment, the antigen presenting cells comprise mature dendritic cells.

According to one embodiment, the antigen presenting cells comprise irradiated dendritic cells.

Thus, according to one embodiment, the DCs are irradiated with about 5-10 Gy, about 10-20 Gy, about 20-30 Gy, about 20-40 Gy, about 20-50 Gy, about 10-50 Gy. According to a specific embodiment, the DCs are irradiated with about 10-50 Gy (e.g. 30 Gy).

Methods of utilizing dendritic cells as APCs are known in the art. Thus, as a non-limiting example, peripheral blood mononuclear cells (PBMCs) may be obtained from a cell donor [e.g. from the same cell donor as the memory T cells]. PBMCs are seeded on a culture plate and incubated for 1-5 hours (e.g. 3 hours) at 37° C. at 5% $CO_2/O_2$ using DC cell medium (e.g. Cellgro DC medium) supplemented with human serum (e.g. 1% human serum) and penicillin/streptomycin (e.g. 1% penicillin/streptomycin). The supernatant cells (comprising T cells) are discarded, and the remaining cells (i.e. adherent cells) are further incubated for 48-96 (e.g. 72 hours) in the same culture conditions with the addition of the cytokines GM-CSF (e.g. 800-1600 IU/ml) and IL-4 (e.g. 750 IU/ml) (available from e.g. Peprotech, Hamburg, Germany). Two to four days (e.g. three days) later, the floating cells are collected (i.e. comprise mostly immature dendritic cells) and are seeded with cytokines for maturation of DCs, e.g. GM-CSF (e.g. 800 IU/ml), IL-4 (e.g. 750 IU/ml), LPS (e.g. from *E. coli* 055:B5 at e.g. 40 ng/ml) and IFN-γ (e.g. 200 IU/ml) (available from e.g. Peprotech, Hamburg, Germany), and incubated overnight. The next day, non-adherent cells may be discarded, and adherent mature DCs may be gently removed using e.g. cold PBS comprising e.g. 2 mM EDTA and 1% HS, after incubation on ice for 10-60 minutes (e.g. 30 minutes), thereby obtaining large cells consisting of mature DC.

In order to present the antigen or antigens on APCs (e.g. mature DCs), the antigen or antigens are co-cultured with the APCs (e.g. DCs) for about for 30 minutes to 3 hours (e.g. 1 hour) at 37° C. at 5% $CO_2/O_2$. For instance, DCs may be loaded with a cocktail of pepmixes (viral peptides) by incubation for about 1 hour at 37° C. at 5% $CO_2/O_2$. The antigen-loaded APCs (e.g. DCs) are then ready to use for generation of Tcm cells from the population of memory T cells according to some embodiments of the invention.

The Tcm cells of the present invention are typically generated by first contacting a population of memory T cells with an antigen or antigens (such as described above) in a culture supplemented with IL-21 (e.g. in an otherwise cytokine-free culture i.e., without the addition of any additional cytokines). This step is typically carried out for about 12-24 hours, about 12-36 hours, about 12-72 hours, 12-96 hours, 12-120 hours, about 24-36 hours, about 24-48 hours, about 24-72 hours, about 36-48 hours, about 36-72 hours, about 48-72 hours, about 48-96 hours, about 48-120 hours, 0.5-1 days, 0.5-2 days, 0.5-3 days, 0.5-5 days, 1-2 days, 1-3 days, 1-5 days, 1-7 days, 1-10 days, 2-3 days, 2-4 days, 2-5 days, 2-6 days, 2-8 days, 3-4 days, 3-5 days, 3-7 days, 4-5 days, 4-8 days, 5-7 days, 6-8 days or 8-10 days or and allows enrichment of antigen reactive cells.

According to a specific embodiment, contacting a population of memory T cells with an antigen or antigens (such as described above) in a culture supplemented with IL-21 (otherwise cytokine-free culture) is effected for 1-5 days (e.g. 3 days).

Contacting a population of memory T cells with an antigen or antigens (such as described above) in a culture supplemented with IL-21 is typically carried out in the presence of about 0.001-3000 IU/ml, 0.01-3000 IU/ml, 0.1-3000 IU/ml, 1-3000 IU/ml, 10-3000 IU/ml, 100-3000 IU/ml, 1000-3000 IU/ml, 0.001-1000 IU/ml, 0.01-1000 IU/ml, 0.1-1000 IU/ml, 1-1000 IU/ml, 10-1000 IU/ml, 100-1000 IU/ml, 250-1000 IU/ml, 500-1000 IU/ml, 750-1000 IU/ml, 10-500 IU/ml, 50-500 IU/ml, 100-500 IU/ml, 250-500 IU/ml, 100-250 IU/ml, 0.1-100 IU/ml, 1-100 IU/ml, 10-100 IU/ml, 30-100 IU/ml, 50-100 IU/ml, 1-50 IU/ml, 10-50 IU/ml, 20-50 IU/ml, 30-50 IU/ml, 1-30 IU/ml, 10-30 IU/ml, 20-30 IU/ml, 10-20 IU/ml, 0.1-10 IU/ml, or 1-10 IU/ml IL-21. According to a specific embodiment, the concentration of IL-21 is 50-500 IU/ml (e.g. 100 IU/ml).

According to a specific embodiment, contacting a population of memory T cells with an antigen or antigens is effected in a cytokine-free culture (e.g. supplemented with only IL-21), such a culture condition enables survival and enrichment of only those cells which undergo stimulation and activation by the antigen or antigens (i.e. of antigen reactive cells) as these cells secrete cytokines (e.g. IL-2) which enable their survival (all the rest of the cells die under these culture conditions).

The ratio of antigen or antigens (e.g. presented on APCs such as antigen pulsed dendritic cells) to memory T cells is typically about 1:2 to about 1:10 such as about 1:4, about 1:5, about 1:6, about 1:8 or about 1:10. According to a specific embodiment, the ratio of antigen or antigens (e.g. presented on APCs) to memory T cells is about 1:2 to about 1:8 (e.g. 1:5).

Next, the resultant memory T cells (i.e. after culture with IL-21) are cultured in the presence of IL-21, IL-15 and/or IL-7 in an antigen free environment (i.e. without the addition of an antigen or antigens) so as to allow proliferation of cells comprising the Tcm phenotype. This step is typically carried out for about 12-24 hours, about 12-36 hours, about 12-72 hours, about 12-96 hours, about 12-120 hours, about 12-240 hours, 24-36 hours, 24-48 hours, about 24-72 hours, 24-96 hours, 24-120 hours, 24-240 hours, about 48-72 hours, about 48-120 hours, about 48-240 hours, about 96-240 hours, about 120-144 hours, about 120-240 hours, about 144-240 hours, 0.5-1 days, 0.5-2 days, 0.5-3 days, 0.5-5 days, 0.5-10 days, 1-2 days, 1-3 days, 1-4 days, 1-6 days, 1-8 days, 1-10 days, 1-15 days, 2-3 days, 2-4 days, 2-5 days, 2-6 days, 2-8 days, 2-10 days, 4-5 days, 4-6 days, 4-8 days, 4-10 days, 5-6 days, 5-7 days, 5-8 days, 5-10 days, 5-15 days, 6-7 days, 6-8 days, 6-10 days, 7-8 days, 7-9 days, 7-10 days, 7-13 days, 7-15 days, 8-10 days, 10-12 days, 10-14 days, 12-14 days, 14-16 days, 14-18 days, 16-18 days or 18-20 days. According to a specific embodiment, the resultant memory T cells (i.e. after culture with IL-21) are cultured in the presence of IL-21, IL-15 and IL-7 in an antigen free environment for about 4-8 days (e.g. 6 days).

This step is typically carried out in the presence of IL-21 at a concentration of about 0.001-3000 IU/ml, 0.01-3000 IU/ml, 0.1-3000 IU/ml, 1-3000 IU/ml, 10-3000 IU/ml, 100-3000 IU/ml, 1000-3000 IU/ml, 0.001-1000 IU/ml, 0.01-1000 IU/ml, 0.1-1000 IU/ml, 1-1000 IU/ml, 10-1000 IU/ml, 100-1000 IU/ml, 250-1000 IU/ml, 500-1000 IU/ml, 750-1000 IU/ml, 10-500 IU/ml, 50-500 IU/ml, 100-500 IU/ml, 250-500 IU/ml, 100-250 IU/ml, 0.1-100 IU/ml, 1-100 IU/ml, 10-100 IU/ml, 30-100 IU/ml, 50-100 IU/ml, 1-50 IU/ml, 10-50 IU/ml, 20-50 IU/ml, 30-50 IU/ml, 1-30 IU/ml, 10-30 IU/ml, 20-30 IU/ml, 10-20 IU/ml, 0.1-10 IU/ml, or 1-10 IU/ml IL-21. According to a specific embodiment, the concentration of IL-21 is 50-500 IU/ml (e.g. 100 IU/ml).

This step is further carried out in the presence of IL-15 at a concentration of about 0.001-3000 IU/ml, 0.01-3000 IU/ml, 0.1-3000 IU/ml, 1-3000 IU/ml, 10-3000 IU/ml, 100-3000 IU/ml, 125-3000 IU/ml, 1000-3000 IU/ml, 0.001-1000 IU/ml, 0.01-1000 IU/ml, 0.1-1000 IU/ml, 1-1000 IU/ml, 10-1000 IU/ml, 100-1000 IU/ml, 125-1000 IU/ml, 250-1000 IU/ml, 500-1000 IU/ml, 750-1000 IU/ml, 10-500 IU/ml, 50-500 IU/ml, 100-500 IU/ml, 125-500 IU/ml, 250-500 IU/ml, 250-500 IU/ml, 125-250 IU/ml, 100-250 IU/ml, 0.1-100 IU/ml, 1-100 IU/ml, 10-100 IU/ml, 30-100 IU/ml, 50-100 IU/ml, 1-50 IU/ml, 10-50 IU/ml, 20-50 IU/ml, 30-50 IU/ml, 1-30 IU/ml, 10-30 IU/ml, 20-30 IU/ml, 10-20 IU/ml, 0.1-10 IU/ml, or 1-10 IU/ml IL-15. According to a specific embodiment the concentration of IL-15 is 50-500 IU/ml (e.g. 125 IU/ml).

This step is further carried out in the presence of IL-7 at a concentration of about 0.001-3000 IU/ml, 0.01-3000 IU/ml, 0.1-3000 IU/ml, 1-3000 IU/ml, 10-3000 IU/ml, 30-3000 IU/ml, 100-3000 IU/ml, 1000-3000 IU/ml, 0.001-1000 IU/ml, 0.01-1000 IU/ml, 0.1-1000 IU/ml, 1-1000 IU/ml, 10-1000 IU/ml, 30-1000 IU/ml, 100-1000 IU/ml, 250-1000 IU/ml, 500-1000 IU/ml, 750-1000 IU/ml, 10-500 IU/ml, 30-500 IU/ml, 50-500 IU/ml, 100-500 IU/ml, 250-500 IU/ml, 100-250 IU/ml, 0.1-100 IU/ml, 1-100 IU/ml, 10-100 IU/ml, 30-100 IU/ml, 50-100 IU/ml, 1-50 IU/ml, 10-50 IU/ml, 20-50 IU/ml, 30-50 IU/ml, 1-30 IU/ml, 10-30 IU/ml, 20-30 IU/ml, 10-20 IU/ml, 0.1-10 IU/ml, or 1-10 IU/ml IL-7. According to a specific embodiment the concentration of IL-7 is 1-100 IU/ml (30 IU/ml).

It will be appreciated that residual antigen or antigens can be present in the cell culture after culture with IL-21 (i.e. in the Tcm proliferation step comprising, for example, the addition of IL-21, IL-15 and IL-7) and thus an antigen free environment relates to a cell culture without the addition of supplementary antigen or antigens.

An additional step which may be carried out in accordance with the present teachings include culturing the resultant memory T cells (i.e. after culture with IL-21) with an antigen or antigens in the presence of IL-21, IL-15 and IL-7 (i.e. prior to generating an antigen free environment). This step is typically carried out for about 12-24 hours, about 12-36 hours, about 12-72 hours, 24-48 hours, 24-36 hours, about 24-72 hours, about 48-72 hours, 1-2 days, 2-3 days, 1-3 days, 2-4 days, 1-5 days or 2-5 days, and is effected at the same doses of IL-21, IL-15 and IL-7 indicated above. According to a specific embodiment, culturing the memory cells with an antigen or antigens in the presence of IL-21, IL-15 and IL-7 is carried out for 12 hours to 4 days (e.g. 1-2 days). According to one embodiment, the total length of time for generating the Tcm cells is about 7, 8, 9, 10, 11 or 12 days (e.g. 9 days).

An additional step which may be carried out in accordance with the present teachings includes selection and removal of activated cells. Such a selection step aids in removal of potential host reactive T cells.

Isolating activated cells may be carried out in a two stage approach. In the first stage activated cells are selected before culturing the cells in the presence of IL-21, IL-15 and IL-7. This first stage is typically carried out after the initial contacting of the memory T cells with an antigen or antigens in the presence of IL-21. This selection process picks only those cells which were activated by antigen or antigens (e.g. express activation markers as described below) and is typically affected about 12-24 hours, about 24-36 hours, about 12-36 hours, about 36-48 hours, about 12-48 hours, about 48-60 hours, about 12-60 hours, about 60-72 hours, about 12-72 hours, about 72-84 hours, about 12-84 hours, about 84-96 hours, about 12-96 hours, after the initial contacting of the memory T cells with an antigen or antigens. According to a specific embodiment, the selection process is effected about 12-24 hours (e.g. 14 hours) after the initial contacting of the memory T cells with an antigen or antigens.

Isolating activated cells may be effected by affinity based purification (e.g. such as by the use of MACS beads, FACS sorter and/or capture ELISA labeling) and may be effected towards any activation markers including cell surface markers such as, but not limited to, CD69, CD44, CD25, CFSE, CD137 or non-cell surface markers such as, but not limited to, IFN-γ and IL-2. Isolating activated cells may also be effected by morphology based purification (e.g. isolating large cells) using any method known in the art (e.g. by FACS). Typically, the activated cells are also selected for expression of $CD8^+$ cells. Furthermore, any combination of the above methods may be utilized to efficiently isolate activated cells.

According to an embodiment of the present invention, selecting for activated cells is effected by selection of CD137+ and/or CD25+ cells.

The second stage of isolation of activated cells is typically carried out at the end of culturing (i.e. after culturing in an antigen free environment with IL-21, IL-15 and IL-7). This stage depletes alloreactive cells by depletion of those cells which were activated following contacting of the central memory T-lymphocyte (Tcm) with irradiated host antigen presenting cells (APCs e.g. dendritic cells). As mentioned above, isolating activated cells may be effected by affinity based purification (e.g. such as by the use of MACS beads, FACS sorter and/or capture ELISA labeling) and may be effected towards any activation markers including cell surface markers such as, but not limited to, CD69, CD44, CD25, CFSE, CD137 or non-cell surface markers such as, but not limited to, IFN-γ and IL-2.

According to an embodiment of the present invention, depleting the alloreactive cells is effected by depletion of CD137+ and/or CD25+ cells.

According to an embodiment of the present invention, depleting the alloreactive cells is effected by culturing the Tcm cells with irradiated host antigen presenting cells (APCs e.g. dendritic cells) for e.g. 12-24 hours (e.g. 16 hours) about 6-9 days (e.g. on day 8) from the beginning of culture (i.e. day 0 being the first day of culturing the memory T cells with an antigen or antigens).

According to one embodiment, isolation of activated cells is carried out only by use of the first stage as discussed above.

According to another embodiment, isolation of activated cells is carried out only by use of the second stage as discussed above.

According to one embodiment, the non-GvHD inducing cells having a central memory T-lymphocyte (Tcm) phenotype of the invention are not naturally occurring and are not a product of nature. These cells are typically produced by ex-vivo manipulation (i.e. exposure to an antigen or antigens in the presence of specific cytokines).

According to one embodiment of the invention, there is provided a method of generating an isolated population of non-GvHD inducing cells comprising a central memory T-lymphocyte (Tcm) phenotype, the cells being veto cells and/or endowed with anti-disease activity, and capable of homing to the lymph nodes following transplantation, the method comprising: (a) treating non-adherent peripheral blood mononuclear cells (PBMCs) with an agent capable of depleting $CD4^+$, $CD56^+$ and $CD45RA^+$ cells so as to obtain a population of memory T cells comprising a $CD45RA^-$ $CD8^+$ phenotype; (b) contacting the population of memory T cells with an antigen or antigens in the presence of IL-21 so as to allow enrichment of antigen reactive cells; and (c) culturing the cells resulting from step (b) in the presence of IL-21, IL-15 and/or IL-7 so as to allow proliferation of cells comprising a Tcm phenotype, thereby generating the isolated population of non-GvHD inducing cells.

According to one embodiment of the invention, there is provided a method of generating an isolated population of non-GvHD inducing cells comprising a central memory T-lymphocyte (Tcm) phenotype, the cells being veto cells and/or endowed with anti-disease activity, and capable of homing to the lymph nodes following transplantation, the method comprising: (a) treating non-adherent peripheral blood mononuclear cells (PBMCs) with an agent capable of depleting $CD4^+$, $CD56^+$ and $CD45RA^+$ cells so as to obtain a population of memory T cells comprising a $CD45RA^-$ $CD8^+$ phenotype; (b) contacting the population of memory T cells with a viral antigen or antigens in the presence of IL-21 so as to allow enrichment of antigen reactive cells; and (c) culturing the cells resulting from step (b) in the presence of IL-21, IL-15 and/or IL-7 so as to allow proliferation of cells comprising the Tcm phenotype, thereby generating the isolated population of non-GvHD inducing cells.

According to one embodiment, in order to obtain memory T cells specific to an antigen or antigens, the antigen/s (e.g. tumor antigen, viral antigen) is administered to the memory T cell donor prior to obtaining memory T cells therefrom (e.g. prior to providing the population of at least 70% memory T cells). Any method of immunizing a cell donor against an antigen in order to elicit an immunogenic response (e.g. generation of memory T cells) may be employed.

The antigen may be administered as is or as part of a composition comprising an adjuvant (e.g. Complete Freund's adjuvant (CFA) or Incomplete Freund's adjuvant (IFA)). According to one embodiment, the antigen is administered to a memory T cell donor once. According to one embodiment, the memory T cell donor receives at least one additional (e.g. boost) administration of the antigen (e.g. 2, 3, 4 or more administrations). Such an additional administration may be affected 1, 3, 5, 7, 10, 12, 14, 21, 30 days or more following the first administration of the antigen.

Additional methods of immunizing a subject towards a tumor antigen which can be used with some embodiments of the invention (e.g. cell based vaccines such as peptide-specific DC vaccines, DC vaccines against undefined epitopes, using leukemia-derived DCs for vaccination, GVAX® platform) are described in Alatrash G. and Molldrem J., *Expert Rev Hematol.* (2011) 4(1): 37-50, incorporated herein by reference.

In order to further enrich the memory T cells against a particular antigen/s and to deplete alloreactive clones from the memory T cell pool, the memory T cells may be further contacted with the same antigen or antigens (e.g. the same antigen as administered to the cell donor), as described hereinabove.

The above describe protocols are typically used for non-syngeneic applications and therefore the memory T cells or PBMC used are typically allogeneic with respect to a subject (e.g. from an allogeneic donor). Likewise, in cases in which a xenogeneic applications may be beneficial, the memory T cells or PBMC used may be of a xenogeneic origin as discussed below.

However, in cases in which a syngeneic applications may be beneficial, the memory T cells or PBMC used may be autologous with respect to a subject (e.g. from the subject). Such determinations are well within the capability of one of skill in the art, especially in view of the disclosure provided.

Thus, as mentioned, the memory T cells or PBMC may be syngeneic or non-syngeneic with respect to a subject.

As used herein, the term "syngeneic" cells refer to cells which are essentially genetically identical with the subject or essentially all lymphocytes of the subject. Examples of syngeneic cells include cells derived from the subject (also referred to in the art as an "autologous"), from a clone of the subject, or from an identical twin of the subject.

As used herein, the term "non-syngeneic" cells refer to cells which are not essentially genetically identical with the subject or essentially all lymphocytes of the subject, such as allogeneic cells or xenogeneic cells.

As used herein, the term "allogeneic" refers to cells which are derived from a donor who is of the same species as the subject, but which is substantially non-clonal with the subject. Typically, outbred, non-zygotic twin mammals of the same species are allogeneic with each other. It will be appreciated that an allogeneic cell may be HLA identical, partially HLA identical or HLA non-identical (i.e. displaying one or more disparate HLA determinant) with respect to the subject.

According to one embodiment, the cell donor is a human being.

As used herein, the term "xenogeneic" refers to a cell which substantially expresses antigens of a different species relative to the species of a substantial proportion of the lymphocytes of the subject. Typically, outbred mammals of different species are xenogeneic with each other.

The present invention envisages that xenogeneic cells are derived from a variety of species. Thus, according to one embodiment, the cells may be derived from any mammal. Suitable species origins for the cells comprise the major domesticated or livestock animals and primates. Such animals include, but are not limited to, porcines (e.g. pig), bovines (e.g., cow), equines (e.g., horse), ovines (e.g., goat, sheep), felines (e.g., *Felis domestica*), canines (e.g., *Canis domestica*), rodents (e.g., mouse, rat, rabbit, guinea pig, gerbil, hamster), and primates (e.g., chimpanzee, rhesus monkey, macaque monkey, marmoset).

Cells of xenogeneic origin (e.g. porcine origin) are preferably obtained from a source which is known to be free of zoonoses, such as porcine endogenous retroviruses. Similarly, human-derived cells or tissues are preferably obtained from substantially pathogen-free sources.

Thus, the source of the memory T cells or PBMCs will be determined with respect to the intended use of the cells (see further details hereinbelow) and is well within the capability of one skilled in the art, especially in light of the detailed disclosure provided herein.

The use of veto cells is especially beneficial in situations in which there is a need to eliminate graft rejection and overcome graft versus host disease (GvHD), such as in transplantation of allogeneic or xenogeneic cells or tissues.

As mentioned above, the veto cells of the invention are further endowed with anti-disease activity and are therefore beneficial in situations in which a subject, e.g. transplanted subject, has a disease or condition (e.g. malignant, viral, bacterial, fungal, autoimmune or allergic disease or condition), pre- or post-transplantation (e.g. before immune reconstitution is established).

Thus, according to another aspect of the present invention, there is provided a method of treating a disease in a subject in need thereof, the method comprising administering to the subject a therapeutically effective amount of the isolated population of non-GvHD inducing cells of some embodiments of the invention (i.e. Tcm cells), thereby treating the disease in the subject.

According to another aspect of the present invention, there is provided a method of treating a subject in need of a cell or tissue transplantation, the method comprising: (a) transplanting a cell or tissue transplant into the subject; and (b) administering to the subject a therapeutically effective amount of the isolated population of non-GvHD inducing cells of some embodiments of the invention (i.e. Tcm cells), thereby treating the subject in need of the cell or tissue transplantation.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "subject" or "subject in need thereof" refers to a mammal, preferably a human being, male or female at any age that is in need of a cell or tissue transplantation or suffers from a disease which may be treated with the Tcm cells. Typically the subject is in need of cell or tissue transplantation (also referred to herein as recipient) due to a disorder or a pathological or undesired condition, state, or syndrome, or a physical, morphological or physiological abnormality which is amenable to treatment via cell or tissue transplantation. Examples of such disorders are provided further below.

As used herein, the term "a therapeutically effective amount" is an amount of Tcm cells efficient for tolerization (i.e. veto effect), anti-disease effect, anti-tumor effect and/or immune reconstitution without inducing GvHD. Since the Tcm cells of the present invention home to the lymph nodes following transplantation, lower amounts of cells (compared to the dose of cells previously used, see for example WO 2001/049243) may be needed to achieve the beneficial effect/s of the cells (e.g. tolerization, anti-disease, anti-tumor effect and/or immune reconstitution). It will be appreciated that lower levels of immunosuppressive drugs (discussed below) may be needed in conjunction with the Tcm cells of the present invention (such as exclusion of rapamycin from the therapeutic protocol).

Determination of the therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

For example, in case of cell transplantation the number of Tcm cells infused to a recipient should be more than $1 \times 10^4$/Kg body weight. The number of Tcm cells infused to a recipient should typically be in the range of $1 \times 10^3$/Kg body weight to $1 \times 10^4$/Kg body weight, range of $1 \times 10^4$/Kg body weight to $1 \times 10^5$/Kg body weight, range of $1 \times 10^4$/Kg body weight to $1 \times 10^6$/Kg body weight, range of $1 \times 10^4$/Kg body weight to $10 \times 10^7$/Kg body weight, range of $1 \times 10^4$/Kg body weight to $1 \times 10^8$/Kg body weight, range of $1 \times 10^3$/Kg body weight to $1 \times 10^5$/Kg body weight, range of $1 \times 10^4$/Kg body weight to $1 \times 10^6$/Kg body weight, range of $1 \times 10^6$/Kg body weight to $10 \times 10^7$/Kg body weight, range of $1 \times 10^5$/Kg body weight to $10 \times 10^7$/Kg body weight, range of $1 \times 10^6$/Kg body weight to $1 \times 10^8$/Kg body weight. According to a specific embodiment, the number of Tcm cells infused to a recipient should be in the range of $1 \times 10^5$/Kg body weight to $10 \times 10^7$/Kg body weight.

Thus, the method of the present invention may be applied to treat any disease such as, but not limited to, a malignant disease, a disease associated with transplantation of a graft (e.g. graft rejection, graft versus host disease), an infectious disease (e.g. viral disease, fungal disease or a bacterial disease), an inflammatory disease, an autoimmune disease and/or an allergic disease or condition.

According to one embodiment, the subject has a malignant disease.

Malignant diseases (also termed cancers) which can be treated by the method of some embodiments of the invention can be any solid or non-solid tumor and/or tumor metastasis.

Examples of cancer include, but are not limited to, carcinoma, lymphoma, blastoma, sarcoma, and leukemia. More particular examples of such cancers include squamous cell cancer, soft-tissue sarcoma, Kaposi's sarcoma, melanoma, lung cancer (including small-cell lung cancer, non-small-cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, rectal cancer, endometrial or uterine carcinoma, carcinoid carcinoma, salivary gland carcinoma, kidney or renal cancer, liver cancer, prostate cancer, vulval cancer, thyroid cancer, hepatic carcinoma, mesothelioma, multiple myeloma, post-transplant lymphoproliferative disorder (PTLD), and various types of head and neck cancer (e.g. brain tumor). The cancerous conditions amenable for treatment of the invention include metastatic cancers.

According to one embodiment, the malignant disease is a hematological malignancy. Exemplary hematological malignancies include, but are not limited to, leukemia [e.g., acute lymphatic, acute lymphoblastic, acute lymphoblastic pre-B cell, acute lymphoblastic T cell leukemia, acute-megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia, T-cell acute lymphocytic leukemia (T-ALL) and B-cell chronic lymphocytic leukemia (B-CLL)] and lymphoma [e.g., Hodgkin's disease, non-Hodgkin's lymphoma, Burkitt, cutaneous T cell, histiocytic, lymphoblastic, T cell, thymic, B cell, including low grade/follicular; small lymphocytic (SL) NHL; intermediate grade/follicular NHL; intermediate grade diffuse NHL; high grade immunoblastic NHL; high grade lymphoblastic NHL; high-grade small non-cleaved cell NHL; bulky disease NHL; mantle cell lymphoma; AIDS-related lymphoma; and Waldenstrom's Macroglobulinemia].

According to a specific embodiment, the malignant disease is a leukemia, a lymphoma, a myeloma, a melanoma, a sarcoma, a neuroblastoma, a colon cancer, a colorectal cancer, a breast cancer, an ovarian cancer, an esophageal cancer, a synovial cell cancer, a hepatic cancer and a pancreatic cancer.

According to one embodiment, the subject has a non-malignant disease.

According to one embodiment, the non-malignant disease is an organ dysfunction or failure, a hematologic disease, a graft related disease, an infectious disease, an inflammatory disease, an autoimmune disease, an allergic disease, a trauma and an injury.

Inflammatory diseases—Include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189); systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydenham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydenham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Specific types of viral pathogens causing infectious diseases treatable according to the teachings of the present invention include, but are not limited to, retroviruses, circoviruses, parvoviruses, papovaviruses, adenoviruses, herpesviruses, iridoviruses, poxviruses, hepadnaviruses, picornaviruses, caliciviruses, togaviruses, flaviviruses, reoviruses, orthomyxoviruses, paramyxoviruses, rhabdoviruses, bunyaviruses, coronaviruses, arenaviruses, and filoviruses.

Specific examples of viral infections which may be treated according to the teachings of the present invention include, but are not limited to, those caused by human immunodeficiency virus (HIV)-induced acquired immunodeficiency syndrome (AIDS), influenza, rhinoviral infection, viral meningitis, Epstein-Barr virus (EBV) infection, hepatitis A, B or C virus infection, measles, papilloma virus infection/warts, cytomegalovirus (CMV) infection, Herpes simplex virus infection, yellow fever, Ebola virus infection, rabies, Adenovirus (Adv), cold viruses, flu viruses, Japanese encephalitis, polio, respiratory syncytial, rubella, smallpox, varicella zoster, rotavirus, West Nile virus and zika virus.

Specific examples of bacterial infections which may be treated according to the teachings of the present invention include, but are not limited to, those caused by anthrax; gram-negative bacilli, chlamydia, diptheria, haemophilus influenza, *Helicobacter pylori*, malaria, *Mycobacterium tuberculosis*, pertussis toxin, pneumococcus, rickettsiae, *staphylococcus*, *streptococcus* and tetanus.

Specific examples of superbug infections (e.g. multi-drug resistant bacteria) which may be treated according to the teachings of the present invention include, but are not limited to, those caused by *Enterococcus faecium*, *Clostridium difficile, Acinetobacter baumannii, Pseudomonas aeruginosa*, and Enterobacteriaceae (including *Escherichia coli, Klebsiella pneumoniae, Enterobacter* spp.).

Specific examples of fungal infections which may be treated according to the teachings of the present invention include, but are not limited to, those caused by *candida, coccidiodes, cryptococcus, histoplasma, leishmania, plasmodium*, protozoa, parasites, schistosomae, tinea, *toxoplasma*, and *Trypanosoma cruzi*.

Graft Rejection Diseases

According to other embodiment, the disease is associated with transplantation of a graft. Examples of diseases associated with transplantation of a graft include, but are not limited to, graft rejection, chronic graft rejection, subacute graft rejection, hyperacute graft rejection, acute graft rejection, allograft rejection, xenograft rejection and graft-versus-host disease (GVHD).

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Non-Malignant Hematologic Disease

Examples of Non-malignant hematologic diseases include, but are not limited to, anemia, bone marrow disorders, deep vein thrombosis/pulmonary embolism, diamond blackfan anemia, hemochromatosis, hemophilia, immune hematologic disorders, iron metabolism disorders, sickle cell disease, thalassemia, thrombocytopenia and Von Willebrand disease.

In order to enhance the anti-disease activity of the Tcm cells, it is beneficial to select an antigen or antigens associated with the disease to be treated and to generate antigen specific Tcm cells for treatment.

Thus, according to one embodiment, the method comprises: (a) analyzing a biological sample of a subject for the presence of an antigen or antigens associated with the disease; (b) generating an isolated population of non-GvHD inducing cells according to the method of some embodiments of the invention towards the antigen or antigens associated with the disease so as to allow enrichment of antigen reactive cells; and (c) administering to the subject a therapeutically effective amount of the isolated population of non-GvHD inducing cells of (b), thereby treating the disease in the subject.

As used herein "a biological sample" refers to a sample of fluid or tissue sample derived from a subject. Examples of "biological samples" include but are not limited to whole blood, serum, plasma, cerebrospinal fluid, urine, lymph fluids, tissue biopsy, and various external secretions of the respiratory, intestinal and genitourinary tracts, tears, saliva, milk as well as white blood cells, tissues, cell culture e.g., primary culture.

Methods of obtaining such biological samples are known in the art including but not limited to standard blood retrieval procedures, urine collection, and lumbar puncture.

Determining the presence of an antigen or antigens in a biological sample can be carried out using any method known in the art, e.g. by serology (testing for the presence of a pathogen), bacterial culture, bacterial susceptibility testing, tests for fungi, viruses, mycobacteria (AFB testing) and/or parasites, electrophoresis, enzyme linked immunosorbent assay (ELISA), western blot analysis and Fluorescence activated cell sorting (FACS).

Once analysis is made, the antigen or antigens are selected and Tcm cells are generated from a population of memory T cells, as discussed above, using the antigen or antigens specific for the disease (e.g. tumor antigens, viral antigens, bacterial antigens, etc.) and are administered to the subject for treatment.

As discussed above, the Tcm cells of the invention are endowed with veto activity. Accordingly, the Tcm cells of the present invention may be used as adjuvant therapy for a cell or tissue transplant. As the Tcm cells of the present invention are also endowed with anti-disease activity the method of the present invention can furthermore be advantageously applied towards treating a disease in a subject while concomitantly facilitating engraftment of a transplant of cells or tissues.

As used herein, the phrase "cell or tissue transplantation" refers to a bodily cell (e.g. a single cell or a group of cells) or tissue (e.g. solid tissues/organs or soft tissues, which may be transplanted in full or in part). Exemplary tissues or organs which may be transplanted according to the present teachings include, but are not limited to, liver, pancreas, spleen, kidney, heart, lung, skin, intestine and lymphoid/hematopoietic tissues (e.g. lymph node, Peyer's patches thymus or bone marrow). Exemplary cells which may be transplanted according to the present teachings include, but are not limited to, immature hematopoietic cells, including stem cells, cardiac cells, hepatic cells, pancreatic cells, spleen cells, pulmonary cells, brain cells, nephric cells, intestine/gut cells, ovarian cells, skin cells, (e.g. isolated population of any of these cells). Furthermore, the present invention also contemplates transplantation of whole organs, such as for example, kidney, heart, liver or skin.

Depending on the application, the method may be effected using a cell or tissue which is syngeneic or non-syngeneic with the subject.

According to an embodiment of the present invention, both the subject and the donor are humans.

Depending on the application and available sources, the cells or tissues of the present invention may be obtained from a prenatal organism, postnatal organism, an adult or a cadaver donor. Moreover, depending on the application needed the cells or tissues may be naïve or genetically modified. Such determinations are well within the ability of one of ordinary skill in the art.

Any method known in the art may be employed to obtain a cell or tissue (e.g. for transplantation).

Transplanting the cell or tissue into the subject may be effected in numerous ways, depending on various parameters, such as, for example, the cell or tissue type; the type, stage or severity of the recipient's disease (e.g. organ failure); the physical or physiological parameters specific to the subject; and/or the desired therapeutic outcome.

Transplanting a cell or tissue transplant of the present invention may be effected by transplanting the cell or tissue transplant into any one of various anatomical locations, depending on the application. The cell or tissue transplant may be transplanted into a homotopic anatomical location (a normal anatomical location for the transplant), or into an ectopic anatomical location (an abnormal anatomical location for the transplant). Depending on the application, the cell or tissue transplant may be advantageously implanted under the renal capsule, or into the kidney, the testicular fat, the sub cutis, the omentum, the portal vein, the liver, the spleen, the heart cavity, the heart, the chest cavity, the lung, the skin, the pancreas and/or the intra abdominal space.

For example, a liver tissue according to the present teachings may be transplanted into the liver, the portal vein, the renal capsule, the sub-cutis, the omentum, the spleen, and the intra-abdominal space. Transplantation of a liver into various anatomical locations such as these is commonly practiced in the art to treat diseases amenable to treatment via hepatic transplantation (e.g. hepatic failure). Similarly, transplanting a pancreatic tissue according to the present invention may be advantageously effected by transplanting the tissue into the portal vein, the liver, the pancreas, the testicular fat, the sub-cutis, the omentum, an intestinal loop (the subserosa of a U loop of the small intestine) and/or the intra-abdominal space. Transplantation of pancreatic tissue may be used to treat diseases amenable to treatment via pancreatic transplantation (e.g. diabetes) Likewise, transplantation of tissues such as a kidney, a heart, a lung or skin tissue may be carried out into any anatomical location described above for the purpose of treating recipients suffering from, for example, renal failure, heart failure, lung failure or skin damage (e. g., burns). In cases in which isolated cells are transplanted, such cells may be administered via, for example, an intravenous route, an intratracheal route, an intraperitoneal route, or an intranasal route.

The method of the present invention may also be used, for example, for treating a recipient suffering from a disease requiring immature hematopoietic cell transplantation.

In the latter case, immature autologous, allogeneic or xenogeneic hematopoietic cells (including stem cells) which can be derived, for example, from bone marrow, mobilized peripheral blood (by for example leukapheresis), fetal liver, yolk sac and/or cord blood of the donor can be transplanted to a recipient suffering from a disease. According to one embodiment, the immature hematopoietic cells are T-cell depleted CD34+ immature hematopoietic cells, Such a disease includes, but is not limited to, leukemia [e.g., acute lymphatic, acute lymphoblastic leukemia (ALL), acute lymphoblastic pre-B cell, acute lymphoblastic T cell leukemia, acute-megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, acute myelocytic leukemia (AML) or chronic myelocytic leukemia (CML), hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia, acute nonlymphoblastic leukemia (ANLL), T-cell acute lymphocytic leukemia (T-ALL) and B-cell chronic lymphocytic leukemia (B-CLL)], lymphoma (e.g., Hodgkin's disease, non-Hodgkin's lymphoma, B cell, Burkitt, cutaneous T cell, histiocytic, lymphoblastic, T cell, thymic), severe combined immunodeficiency syndromes (SCID), including adenosine deaminase (ADA), osteopetrosis, aplastic anemia, Gaucher's disease, thalassemia and other congenital or genetically-determined hematopoietic abnormalities.

It will be appreciated that the immature autologous, allogeneic or xenogeneic hematopoietic cells of the present invention may be transplanted into a recipient using any method known in the art for cell transplantation, such as but not limited to, cell infusion (e.g. I.V.) or via an intraperitoneal route.

Optionally, when transplanting a cell or tissue transplant of the present invention into a subject having a defective organ, it may be advantageous to first at least partially remove the failed organ from the subject so as to enable optimal development of the transplant, and structural/functional integration thereof with the anatomy/physiology of the subject.

According to one embodiment, the cell or tissue transplant is derived from an allogeneic donor. According to one embodiment, the cell or tissue transplant is derived from an HLA identical allogeneic donor or from an HLA non-identical allogeneic donor. According to one embodiment, the cell or tissue transplant is derived from a xenogeneic donor.

According to one embodiment, the cell or tissue transplant and the isolated population of Tcm cells are derived from the same (e.g. non-syngeneic) donor.

According to one embodiment, the cell or tissue transplant and the isolated population of Tcm cells are derived from different (e.g. non-syngeneic) donors. Accordingly, the cell or tissue transplant may be non-syngeneic with the Tcm cells.

According to one embodiment, the immature hematopoietic cells and the isolated population of Tcm cells are derived from the same (e.g. non-syngeneic) donor.

According to one embodiment, the immature hematopoietic cells and the isolated population of Tcm cells are derived from different (e.g. non-syngeneic) donors. Accordingly, the immature hematopoietic cells may be non-syngeneic with the Tcm cells.

The method of the present invention also envisions co-transplantation of several organs (e.g. cardiac and pulmonary tissues) in case the subject may be beneficially effected by such a procedure.

According to one embodiment, the co-transplantation comprises transplantation of immature hematopoietic cells and a solid tissue/organ or a number of solid organs/tissues.

According to one embodiment, the immature hematopoietic cells and the solid organ or obtained from the same donor.

According to another embodiment, the immature hematopoietic cells and the solid organ/tissue or organs/tissue are obtained from different (e.g. non-syngeneic) donors.

According to one embodiment, the immature hematopoietic cells are transplanted prior to, concomitantly with, or following the transplantation of the solid organ.

According to an embodiment, hematopoietic chimerism is first induced in the subject by transplantation of immature hematopoietic cells in conjunction with the Tcm cells of the present invention, leading to tolerance of other tissues/organs transplanted from the same donor.

According to an embodiment, the Tcm cells of the present invention are used per se for reduction of rejection of transplanted tissues/organs organs transplanted from the same donor.

Following transplantation of the cell or tissue transplant into the subject according to the present teachings, it is advisable, according to standard medical practice, to monitor the growth functionality and immuno-compatability of the organ according to any one of various standard art techniques. For example, the functionality of a pancreatic tissue transplant may be monitored following transplantation by standard pancreas function tests (e.g. analysis of serum levels of insulin). Likewise, a liver tissue transplant may be monitored following transplantation by standard liver function tests (e.g. analysis of serum levels of albumin, total protein, ALT, AST, and bilirubin, and analysis of blood-clotting time). Structural development of the cells or tissues may be monitored via computerized tomography, or ultrasound imaging.

Depending on the transplantation context, in order to facilitate engraftment of the cell or tissue transplant, the method may further advantageously comprise conditioning the subject under sublethal, lethal or supralethal conditions prior to the transplanting.

As used herein, the terms "sublethal", "lethal", and "supralethal", when relating to conditioning of subjects of the present invention, refer to myelotoxic and/or lymphocytotoxic treatments which, when applied to a representative population of the subjects, respectively, are typically: non-lethal to essentially all members of the population; lethal to some but not all members of the population; or lethal to essentially all members of the population under normal conditions of sterility.

According to some embodiments of the invention, the sublethal, lethal or supralethal conditioning comprises a total body irradiation (TBI), total lymphoid irradiation (TLI, i.e. exposure of all lymph nodes, the thymus, and spleen), partial body irradiation (e.g. specific exposure of the lungs, kidney, brain etc.), myeloablative conditioning and/or non-myeloablative conditioning, e.g. with different combinations including, but not limited to, co-stimulatory blockade, chemotherapeutic agent and/or antibody immunotherapy. According to some embodiments of the invention, the conditioning comprises a combination of any of the above described conditioning protocols (e.g. chemotherapeutic agent and TBI, co-stimulatory blockade and chemotherapeutic agent, antibody immunotherapy and chemotherapeutic agent, etc.).

According to one embodiment, the TBI comprises a single or fractionated irradiation dose within the range of 0.5-1 Gy, 0.5-1.5 Gy, 0.5-2.5 Gy, 0.5-5 Gy, 0.5-7.5 Gy, 0.5-10 Gy, 0.5-15 Gy, 1-1.5 Gy, 1-2 Gy, 1-2.5 Gy, 1-3 Gy, 1-3.5 Gy, 1-4 Gy, 1-4.5 Gy, 1-1.5 Gy, 1-7.5 Gy, 1-10 Gy, 2-3 Gy, 2-4 Gy, 2-5 Gy, 2-6 Gy, 2-7 Gy, 2-8 Gy, 2-9 Gy, 2-10 Gy, 3-4 Gy, 3-5 Gy, 3-6 Gy, 3-7 Gy, 3-8 Gy, 3-9 Gy, 3-10 Gy, 4-5 Gy, 4-6 Gy, 4-7 Gy, 4-8 Gy, 4-9 Gy, 4-10 Gy, 5-6 Gy, 5-7 Gy, 5-8 Gy, 5-9 Gy, 5-10 Gy, 6-7 Gy, 6-8 Gy, 6-9 Gy, 6-10 Gy, 7-8 Gy, 7-9 Gy, 7-10 Gy, 8-9 Gy, 8-10 Gy, 10-12 Gy or 10-15 Gy.

According to a specific embodiment, the TBI comprises a single or fractionated irradiation dose within the range of 1-7.5 Gy.

According to one embodiment, the conditioning is effected by conditioning the subject under supralethal conditions, such as under myeloablative conditions.

Alternatively, the conditioning may be effected by conditioning the subject under lethal or sublethal conditions, such as by conditioning the subject under myeloreductive conditions or non-myeloablative conditions.

According to one embodiment, the conditioning is effected by conditioning the subject with a myeloablative drug (e.g. Busulfan or Melfaln) or a non-myeloablative drug (e.g. Cyclophosphamide and or Fludarabin).

Examples of conditioning agents which may be used to condition the subject include, without limitation, irradiation, pharmacological agents, and tolerance-inducing cells (as described herein).

Examples of pharmacological agents include myelotoxic drugs, lymphocytotoxic drugs and immunosuppressant drugs (discussed in detail below).

Examples of myelotoxic drugs include, without limitation, busulfan, dimethyl mileran, melphalan and thiotepa.

Additionally or alternatively, the method may further comprise conditioning the subject with an immunosuppressive regimen prior to, concomitantly with, or following transplantation of the cell or tissue transplant.

Examples of suitable types of immunosuppressive regimens include administration of immunosuppressive drugs, tolerance inducing cell populations (e.g. Tcm cells, as described in detail hereinabove), and/or immunosuppressive irradiation.

Ample guidance for selecting and administering suitable immunosuppressive regimens for transplantation is provided in the literature of the art (for example, refer to: Kirkpatrick C H. and Rowlands D T Jr., 1992. JAMA. 268, 2952; Higgins R M. et al., 1996. Lancet 348, 1208; Suthanthiran M. and Strom T B., 1996. New Engl. J. Med. 331, 365; Midthun D E. et al., 1997. Mayo Clin Proc. 72, 175; Morrison V A. et al., 1994. Am J Med. 97, 14; Hanto D W., 1995. Annu Rev Med. 46, 381; Senderowicz A M. et al., 1997. Ann Intern Med. 126, 882; Vincenti F. et al., 1998. New Engl. J. Med. 338, 161; Dantal J. et al. 1998. Lancet 351, 623).

Preferably, the immunosuppressive regimen consists of administering at least one immunosuppressant agent to the subject.

Examples of immunosuppressive agents include, but are not limited to, Tacrolimus (also referred to as FK-506 or fujimycin, trade names: Prograf, Advagraf, Protopic), Mycophenolate Mofetil, Mycophenolate Sodium, Prednisone, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF.alpha, blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, tramadol, rapamycin (sirolimus) and rapamycin analogs (such as CCI-779, RAD001, AP23573). These agents may be administered individually or in combination.

Regardless of the transplant type, to avoid graft rejection and graft versus host disease, the method of the present invention utilizes the novel Tcm cells (as described in detail hereinabove).

According to the method of the present invention, these Tcm cells are administered either concomitantly with, prior to, or following the transplantation of the cell or tissue transplant.

The Tcm cells may be administered via any method known in the art for cell transplantation, such as but not limited to, cell infusion (e.g. intravenous) or via an intraperitoneal route.

The Tcm cells of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the Tcm cells accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (Tcm cells) effective to prevent, alleviate or ameliorate symptoms of a disorder (e.g., malignant or non-malignant disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide ample levels of the active ingredient which are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ± 10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Animals

Females 6-to 12-week-old BALB/c, FVB, C57BL/6 and BALB/c-NUDE mice were obtained from Harlan Laboratories. Congenic B6.SJL, C57BL/6-Tg(CAG-OVA)916Jen/J mice (OVA-expressing mice) and OT1 mice (that express a transgenic (Tg) TCR designed to recognize ovalbumin (OVA) residues 257-264 in the context of H2Kb MHC-I) and OT1/Rag-/CD45.1 were bred at the Weizmann Institute Animal Center. All mice were kept in small cages (5 animals in each cage) and fed sterile food and acid water. The Weizmann Institute of Science Institutional Animal Care and Use Committee approved these studies.

Generation of Veto Cells from Murine Memory T Cells

OT1 mice that express a transgenic (Tg) TCR designed to recognize ovalbumin (OVA) residues 257-264 in the context of H2Kb MHC-I were used. These mice served as the donors of veto Tcm cells. Prior to harvest of these OT1 CD8 T cells, mice were immunized with OVA-peptide mixed with Complete Freund's adjuvant (CFA) and given a boost of immunization 14 days after initial challenge using OVA-peptide+ Incomplete Freund's adjuvant (IFA). Seven to fourteen days after immunization mice were sacrificed, their spleens and lymph nodes removed and crushed, and magnetic beads sorting utilized to isolate the memory cells ($CD8^+CD44^+$) from the general $CD8^+$ cell-pool. Resultant population was subjected to third-party stimulation by co-culture with irradiated splenocytes generated from spleens of OVA-expressing mice, under cytokine deprivation. Sixty-hours after co-culture initiation, hIL-15 (10 ng/ml) was added to the culture in order to push cells to express a Tcm like phenotype as described below for wild-type (WT) Tcm i.e. the previously described veto Tcm cells, which are prepared from whole spleen or peripheral blood mononuclear cells as substantiated previously [Ophir, E. (2013), supra]).

Generation of Viral Peptide Loaded Human Dendritic Cells

Figure 4B:
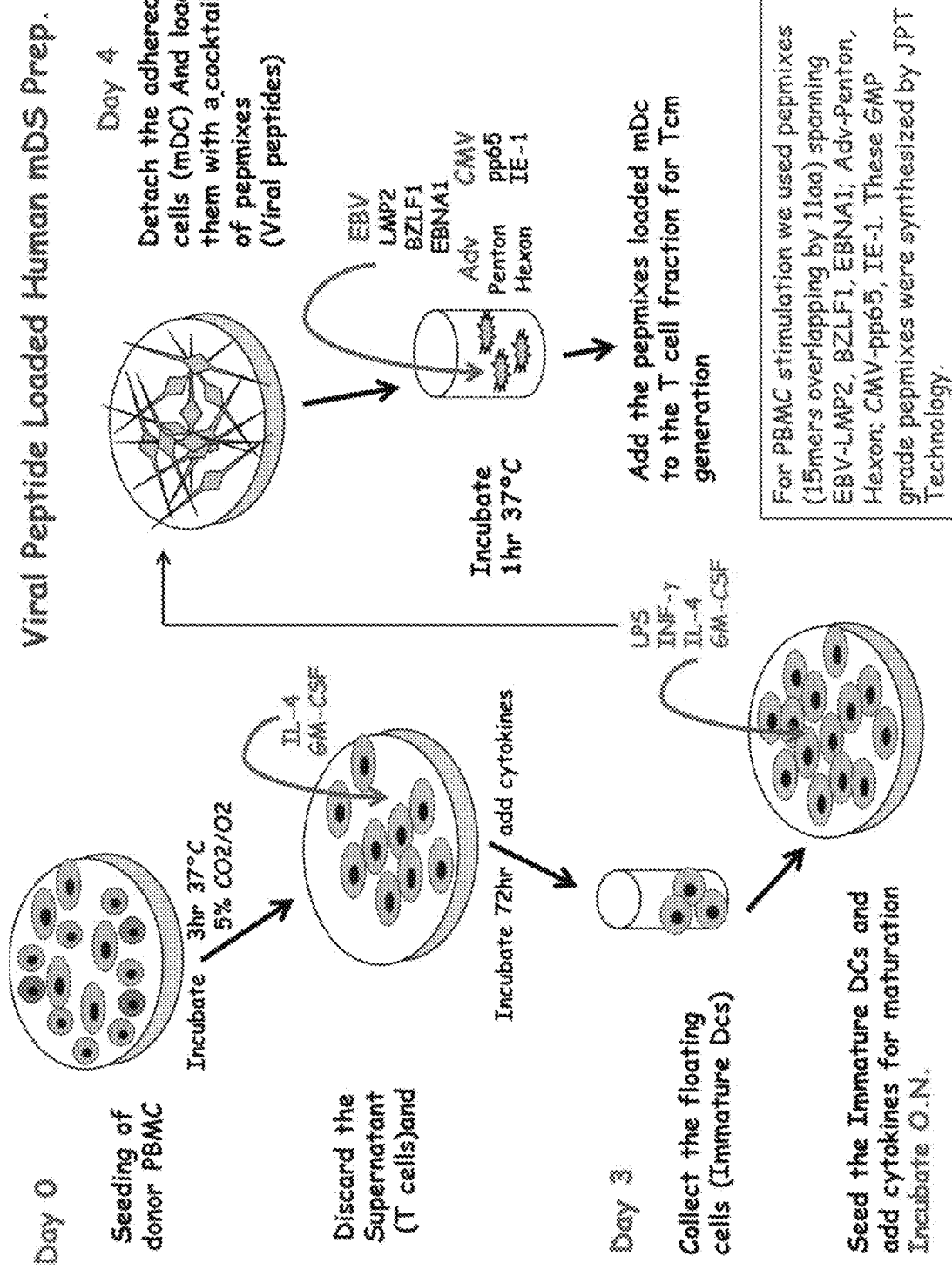
FIG. 4B is a schematic representation of the generation of viral peptide loaded human mature dendritic cells.

Viral peptide loaded human dendritic cells (DCs) were prepared as illustrated in FIG. 4B. In short, Donor peripheral blood mononuclear cells (PBMCs) were seeded on a culture plate and incubated for 3 hours at 37° C. at 5% $CO_2/O_2$. The supernatant cells (comprising T cells) were discarded, and the adhered cells, were further incubated for 72 hours with the addition of the cytokines IL-4 and GM-CSF (in the same culture conditions). Three days later, the floating cells were collected (immature dendritic cells), seeded and incubated over night with the following cytokines INF-γ, IL-4, GM-CSF and LPS for maturation of DCs. On day 4, the adhered cells (mature DC, i.e. mDC) were detached loaded with a cocktail of viral peptides and incubated for 1 hour at 37° C. The viral cocktail comprises 7 pepmixes of EBV, CMV and Adenovirus (Adv). Pepmixes are 15 mers overlapping by 11 amino acids of the entire protein sequence of the antigen of interest purchased from JPT Technologies (Berlin, Germany). Pepmixes spanning EBV (LMP2, BZLF1, EBNA1), Adv-(Penton, Hexon) and CMV-(pp65, IE-1) were used. The viral peptide loaded human mDCs were then irradiated 30 Gy and added to the T cell fraction as discussed below.

Generation of Human Anti-Third Party Tcm Cells Using Viral Peptides

Anti-third party human veto cells were generated by first depleting peripheral blood mononuclear cells (PBMC), obtained from a cell donor, of $CD4^+$ and $CD56^+$ cells (using magnetic cells sorting using magnetic beads obtained from Milteni Biotec.

The remaining population of cells were co-cultured with irradiated (30 Gy) dendritic cells (of the same cell donor), wherein the dendritic cells have been pulsed to express a third party antigen (e.g. viral antigen cocktail including EBV, CMV and Adenovirus). For the first 3 days of culture, the cells were supplemented with IL-21 only, then from day +3 IL-21, IL-15 and IL-7 were added to the culture until day +9.

Generation of Human Veto Tcm Cells from Memory T Cells Using Viral Peptides

Veto cells were generated from human memory cells by first depleting peripheral blood mononuclear cells (PBMC), obtained from a cell donor, of $CD4^+$, $CD56^+$ and $CD45RA^+$ cells (using magnetic cells sorting using magnetic beads obtained from Milteni Biotec). The remaining population of cells comprised $CD8^+CD45RO^+$ memory T cells. Next, the memory $CD8^+CD45RO^+$ T cells were co-cultured with irradiated (30 Gy) dendritic cells (of the same cell donor), wherein the dendritic cells have been pulsed to express an antigen (e.g. viral antigen cocktail including EBV, CMV and Adenovirus). For the first 3 days of culture, the cells were supplemented with IL-21 only, then from day +3 IL-21, IL-15 and IL-7 were added to the culture until day +9.

Generation of Human Veto Tcm Cells from Memory T Cells Using Tumor Peptides

Veto cells are generated from human memory cells by first immunizing the cell donor with a tumor peptide (e.g. BCR-ABL, ELA2, G250/carbonic anhydrase IX, HA-1, HA-2, hTERT, MAGE-1, MUC1, NY-ESO-1, PRAME, PR1, PRTN3, RHAMM and WT-1, or combinations thereof, as discussed in Molldrem J. *Biology of Blood and Marrow Transplantation* (2006) 12:13-18; Alatrash G. and Molldrem J., *Expert Rev Hematol*. (2011) 4(1): 37-50) with Complete Freund's adjuvant (CFA) and given a boost of immunization 14 days after initial challenge using the tumor peptide+ Incomplete Freund's adjuvant (IFA). Next, peripheral blood mononuclear cells (PBMC) are obtained and are depleted of $CD4^+$, $CD56^+$ and $CD45RA^+$ cells (using magnetic cells sorting using magnetic beads obtained from Milteni Biotec). The remaining population of cells comprises $CD8^+CD45RO^+$ memory T cells. Next, the memory $CD8^+CD45RO^+$ T cells are co-cultured with irradiated (30 Gy) dendritic cells (of the same cell donor), wherein the dendritic cells have been pulsed to express the tumor antigen. For the first 3 days of culture, the cells are supplemented with IL-21 only, and then from day +3 IL-21, IL-15 and IL-7 are added to the culture until day +9.

Flow Cytometric Analysis

Fluorescence-activated cell sorting (FACS) analysis was performed using a Becton Dickinson FACScanto II, to determine the level of purity and phenotype of the Tcm cells that were generated i.e. CD8+CD45RO+CD62L+ and CD4−CD56−CD45RA−. Cells were stained in two panels with the following labeled antibodies:

Panel 1: CD8− Fluorescein isothiocyanate (FITC), CD45RO− Phycoerythrin (PE), CD62L− Allophycocyanin (APC), CD56−APC-Cy7, CD3-Brilliant Violet 711, CD16-PE-Cy7 and 7AAD-PerCp.

Panel 2: CD3-Brilliant Violet 711, CD8-FITC, CD45RA-PE-Cy7, CD45RO-APC-Cy7, CD20-PE and 7AAD-PerCp.

Limit Dilution Analysis (LDA) and $^{35}$S-Methionine Killing Assay

In order to evaluate the frequency of residual anti host reactive cells within the anti-$3^{rd}$ party Tcm cultures generated from PBMCs in different stages of purification, such as $CD4^-CD56^-$ (i.e. enriched $CD8^+$ cells) or $CD4^-CD56^-CD45RA^-$ (i.e. memory cells) limit dilution analysis (LDA) was performed in comparison to fresh $CD4^-CD56^-CD19^-$ cells (serving as allogeneic positive control). The three tested cell preparations were cultured against irradiated host PBMCs in an MLR culture for 5 days (i.e. bulk culture) to allow the induction of anti-host activity. Following 5 days, effector cells were harvested from the MLR culture and separated on Ficoll. The effector cells were plated out in different dilutions (range, 1 to 40 000 cells per well) in 96-well round-bottom plates (16 replicates per input number). Irradiated (30 Gy) host stimulators that were used in the bulk MLR were also added to each well. The limiting dilution cultures were used to allow the titration of the end point of anti-host signal and maintained for 7 days in the presence of IL-2 for the amplification of the effectors signal.

Following 7 days, cytotoxic activity was measured in a standard 5-hour assay against $^{35}$S-Methionine-labeled cells. Briefly, concanavalin A—prepared blasts (Sigma, St Louis, Mo.) from the Host that used as target cells, were labeled with $^{35}$S-Methionine and plated together with the various dilutions of the tested induced effector cells. After a 5 hour incubation, the mean radioactivity in the supernatants of 16 replicate samples was calculated, and the percentage of specific lysis was calculated by the following equation: 100×(mean experimental release−mean spontaneous release)/(mean total release−mean spontaneous release). The level of $^{35}$S-methionine released by target cells represents the level of killing which represents the level of anti-host reactivity.

To calculate the frequency from the limiting dilution culture readout, the following equation was used: lny=−fx+lna (which represents the zero-order term of the Poisson distribution), in which y is the percentage of non-responding cultures, x is the number of responding cells per culture, f is the frequency of responding precursors, and a is they intercept theoretically equal to 100%. The mean plus 3 standard deviations of the 16 wells containing the target cells alone was determined as the cutoff value for background radioactivity. Experimental wells were scored positive for lysis when exceeding the cutoff value. The percent responding cultures was defined by calculating the percent of positive cultures. The CTL-p frequency (f) and standard error (SE) were determined from the slope of the line drawn utilizing linear regression analysis of the data.

IFN-γ-Elispot Analysis

The enzyme-linked immunospot (ELISpot) assay, a highly sensitive immunoassay that measures the frequency of cytokine-secreting cells at the single-cell level, was used. Specifically, INF-γ (Interferon-gamma) ELISpot assay was used to evaluate the frequency of residual anti-host reactive cells within the anti-3$^{rd}$ party Tcm cultures, as IFN-γ is produced mainly by activated T cells and NK cells.

In short, the membrane surfaces in a 96-well PVDF membrane microtiter plate were coated with a capture antibody (purified anti-Human INF-γ) that binds a specific epitope of the cytokine (IFN-γ) being assayed. During 16 hours of MLR and stimulation step, various dilutions (at a range of 1 to 40,000 cells per well) of the tested cells were seeded into the wells of the plate along with irradiated anti-host stimulators. These formed a monolayer on the membrane surface of the well. As anti-host-specific cells are activated, these release IFN-γ, which is captured directly on the membrane surface by the immobilized antibody. The IFN-γ is thus "captured" in the area directly surrounding the secreting cell, before it has a chance to diffuse into the culture media, or to be degraded by proteases and bound by receptors on bystander cells. Subsequent detection steps visualize the immobilized IFN-γ as an ImmunoSpot. After washing the wells to remove cells, debris, and media components, a biotinylated antibody specific for Human IFN-γ was added to the wells. This antibody is reactive with a distinct epitope of the IFN-γ cytokine and thus is employed to detect the captured cytokine. Following a wash to remove any unbound biotinylated antibody, the detected cytokine was visualized using streptavidin conjugated to an enzyme horseradish peroxidase (HRP) and a precipitating substrate (e.g., AEC, BCIP/NBT). The colored end product (a red spot, (for HRP) typically represents an individual IFN-γ-producing cell. The spots were counted manually (e.g. with a dissecting microscope) or using an automated reader to capture the microwell images and to analyze spot number and size.

Example 1

TCR Transgenic CD8 Memory T Cells Expanded Against Their Cognate Antigen Markedly Enhance Engraftment of Fully Allogeneic T Cell Depleted BM The possibility that memory T cells might be associated with reduced risk for GvHD has been debated over the past decade. In principle, the memory pool is enriched with anti-viral clones and therefore might contain a reduced level of alloreactive T cells. However, very recently, two major studies which attempted to use CD45RA$^+$ depleted HSCT in leukemia patients reported a significant level of GvHD, even when using post-transplant GvHD prophylaxis [Bleakley M. et al. J Clin Invest. (2015) 125(7):2677-89; Triplett, B. M. et al. Bone Marrow Transplant. (2015) 50(7):968-977]. Thus, depletion of alloreactive clones from the T-cell memory pool by way of anti-third-party T cell activation and expansion may solve the problem of residual GvHD that remains after depletion of CD45RA cells. Moreover, the use of common viral-antigen peptides as third-party stimulation, could potentially create veto Tcm cells that are both depleted of alloreactivity and endowed with anti-viral activity.

To that end, the present inventors have modified the previous protocol for the generation of anti-third party veto Tcm cells, by establishing stimulation using specific peptides against which the TCR of the existing memory T-cell pool is directed. Thus, proof of concept experiments were carried out in murine models, using OT1 mice that express a transgenic (Tg) TCR designed to recognize ovalbumin (OVA) residues 257-264 in the context of H2Kb MHC-I. These mice served as the donors of veto Tcm cells. Prior to harvest of these OT1 CD8 T cells, mice were immunized with OVA-peptide mixed with Complete Freund's adjuvant (CFA) and given a boost of immunization 14 days after initial challenge using OVA-peptide+Incomplete Freund's adjuvant (IFA) (see the illustration in FIG. 1). Seven to fourteen days after immunization mice were sacrificed, their spleens and lymph nodes removed and crushed, and magnetic beads sorting utilized to isolate the memory cells (CD8$^+$CD44$^+$) from the general CD8$^+$ cell-pool. Resultant population was subjected to third-party stimulation by co-culture with irradiated splenocytes generated from spleens of OVA-expressing mice, under cytokine deprivation. Sixty-hours after co-culture initiation, hIL-15 (10 ng/ml) was added to the culture in order to push cells to express a Tcm like phenotype as described above for WT Tcm (i.e. 'regular' Tcm cells, as discussed below).

As shown in FIG. 2A, OT-1 Tcm cells prepared from a starting population of memory cells (CD8$^+$CD44$^+$) were able to enhance engraftment of allogeneic T cell depleted bone marrow transplant, similarly to the chimerism induced by 'regular' anti-third party Tcm cells (i.e. the previously described veto Tcm cells, which are prepared from whole spleen or peripheral blood mononuclear cells as substantiated previously [Ophir, E. (2013), supra]). Taken together these results strongly demonstrate that CD8$^+$CD44$^+$ derived Tcm cells expanded against cognate peptides can indeed induce tolerance, without exerting GvHD.

Example 2

Tcm Veto Cells Generated from CD8 Memory T Cells Offer Marked Veto Activity with Reduced Risk from GVHD Next, the present inventors attempted to obtain Tcm cells from B6-WT memory CD8 T cells following immunization with OVA. To that end, following immunization of C57BL/6 mice, $CD8^+CD44^+$ memory T cells were magnetically sorted and subjected to the same protocol for Tcm generation using all-OVA stimulators. Initially the present inventors wanted to test the capacity of these $CD8^+CD44^+$ Tcm cells to induce GvHD, compared to that of the starting population of $CD8^+CD44^+$ which were previously used in the clinic. It was expected that $CD8^+CD44^+$ Tcm cells would be depleted of alloreactive clones due to the antigenic stimulation using OVA peptide, which selectively activates only those T-cell clones that possess a relevant TCR.

Figure 2D:
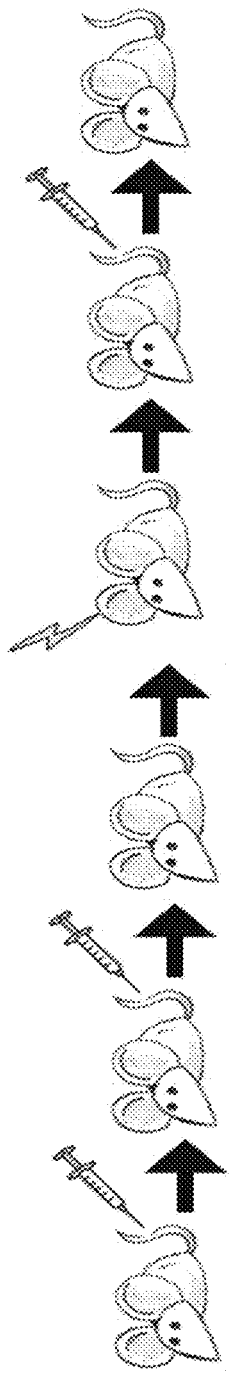
FIG. 2D is a schematic illustration of a reduced intensity conditioning (RIC) model to test tolerance induction by Tcm cells derived from naturally occurring memory cells (e.g. $CD44^+CD8^+$ anti-OVA).

Indeed, it was shown that $CD8^+CD44^+$ Tcm cells do not induce marked GvHD symptoms in animal models, whereas $CD8^+CD44^+$ fresh memory cells which did not undergo third party activation induced significant lethality and weight loss due to GvHD (FIGS. 2B-2C). Next, the present inventors wanted to assess whether these cells were able to induce tolerance in the reduced intensity conditioning (RIC) model (illustrated in FIG. 2D). As can be seen in FIG. 2E, $CD8^+CD44^+$ Tcm exhibited marked enhancement of chimerism following transplantation of C57BL-Nude-BM into Balb/c recipients conditioned with 5 Gy TBI.

Example 3

Generation of Anti-Third Party Human Tcm Cells Using Viral Antigens

The present inventors have previously developed a protocol for the generation of human derived anti-$3^{rd}$ party veto Tcm cells from a $CD4^-CD56^-$ cell starting population with a minimal risk for GvHD, using a two stage magnetic sorting approach for depletion of alloreactivity. This protocol was developed using three cell donors, where the third-party donor was selected so as to insure that none of its HLA class I alleles were shared with the HLA class I alleles of the host, for the purpose of preventing GvHD.

In the current experiments, similar to that described above for the murine proof-of-concept experiments, the present inventors exploited the use of naturally occurring memory-CD8 cells as a starting material for preparation of veto Tcm cells, as these cells have been reported to have a reduced propensity for GvHD induction compared to naïve cells. This option has recently become a reality with the release of GMP-grade CD45RA magnetic beads for depletion of naïve T-cells. As described above and in the 'field and background section' hereinabove, the approach of infusing $CD45RA^-$ cells has been tested in two clinical trials in leukemia patients [Bleakley M. et al. (2015) supra; Triplett, B. M. et al. (2015) supra] however, GvHD was not prevented with some patients exhibiting severe forms of GvHD even if treated with immune suppression after transplantation. These data led the present inventors to assess the possibility that stimulation of CD45RA-depleted CD8 T-cells against specific antigens may completely deplete these cells of all GvH reactivity. Since the TCR of most of the cells in this memory pool are directed against common viral and bacterial antigens and are therefore naturally less likely to be host-alloreactive, the present inventors theorized that viral antigen peptides (e.g. CMV, EBV and Adenovirus) loaded on donor DCs (i.e. of the same cell donor as the Tcm cells) as stimulators could conveniently be used. Using this approach, the benefit of a possible anti-viral activity of these cells in addition to their veto activity may be obtained, which is a particularly attractive attribute for transplantation setup where viral re-activation is a common deleterious occurrence.

To address this assumption, a preliminary experiment was initiated in which the same culture conditions of veto Tcm cells was used except that the stimulation against an antigen was performed against donor DCs pulsed with viral peptide mixtures of three prominent viruses (EBV, CMV and Adenovirus), in place of a third HLA-desperate donor for third-party DCs. Of note, this experiment was started out from the previously described $CD4^-CD56^-$ population (i.e. $CD45RA^+$ cells were not removed). As can be seen in FIGS. 3A-3B, veto Tcm cells grew well in response to this anti-viral stimulation, showing a 10-fold expansion by day +9 with a high percentage (93.2%) of the cells exhibiting a veto Tcm phenotype.

Anti-host reactivity analyzed by limiting dilution analysis (LDA) is shown in FIGS. 3C-3D and relevant parameters summarized in Table 2, below. Results showed that this method afforded a two-log depletion of host-alloreactive clones, similar to the previous results using 'regular' third-party activation against a disparate HLA-donor. These results were further corroborated by IFNγ-Elispot analysis (carried out after the bulk culture) where, upon host activation, fresh cells ($CD4^-CD56^-CD19^-$) produced approximately 25,000 spots/per $10^6$ T-cells no spots could be detected in the veto Tcm cell culture (data not shown).

TABLE 2

Anti-host T-cell depletion before and after generation of veto Tcm cells directed against viral peptides

| Cell Fraction | Cell number seeded for bulk culture vs. host (Day 9) | Cell number harvested after bulk culture (Day 14) | Anti-host CTL-p frequency based on LDA | Total anti-host CTL-p ($\times 10^6$) based on LDA (Normalized to $100 \times 10^6$) | Depletion factor |
|---|---|---|---|---|---|
| Fresh $CD4^-56^-19^-$ | $50 \times 10^6$ | $32.4 \times 10^6$ | 1/2251 | 28,700 | x |
| Anti-viral Tcm $CD4^-56^-$ | $200 \times 10^6$ | $19.4 \times 10^6$ | 1/32,664 | 290 | 98.9 |

Example 4

Generation of Human Veto Cells from Memory T Cells Using Viral Antigens

Next, the present inventors tested the reactivity of Tcm cells grown from a CD45RA-depleted population activated towards viral antigens presented on donor DCs (i.e. of the same cell donor as the Tcm cells) (as illustrated in FIGS. 4A and 4B).

The reactivity of veto Tcm cells grown from this starting population (CD4$^-$CD56$^-$CD45RA$^-$ cells) was tested using the LDA killing assay. As evident from the results, it is clear that the veto cells generated from memory cells do not exert any anti-host reactivity (FIGS. 5A-5C and FIG. 6).

Taken together, these results strongly suggest that the approach of anti-viral peptides as stimulators can be applied to a starting population of responding cells that are CD45RA depleted (e.g. CD4$^-$CD56$^-$CD45RA$^-$ cells), known for their relatively low GvHD propensity. As shown, this cell population could be further diluted of putative anti-host clones upon anti-viral stimulation, which could yield and extremely safe, GvHD-free, cell preparation.

Example 5

Generation of Human Veto Cells from Memory T Cells Using Non-Viral Antigens

The present inventors are generating veto cells from a starting population of memory cells (CD45RA$^-$ cells) stimulated against non-viral peptides including peptides identified with cancer (e.g. solid tumor or hematopoietic malignancy).

As described above, veto cells are generated by subjecting memory T cells (i.e. CD45RA-depleted population) obtained from a donor towards tumor antigens presented on donor DCs.

Alternatively, veto cells are generated by first immunized the cell donor with a tumor peptide (as discussed in the 'general materials and experimental procedures' section above) with Complete Freund's adjuvant (CFA) and given a boost of immunization 14 days after initial challenge using the tumor peptide+Incomplete Freund's adjuvant (IFA). Next, peripheral blood mononuclear cells (PBMC) are obtained from the subject and are depleted of CD4$^+$CD56$^+$ CD45RA$^+$ cells. The remaining population of cells (i.e. CD8$^+$CD45RO$^+$ memory T cells) are co-cultured with tumor antigens presented on donor DCs.

These cells can be further used for the therapeutic elimination of residual cancer cells.

Example 6

Good Manufacturing Practice (GMP) Protocol for Large Scale Generation of Anti-Viral Central Memory CD8 Veto T Cells (Tcms)

Figure 7:
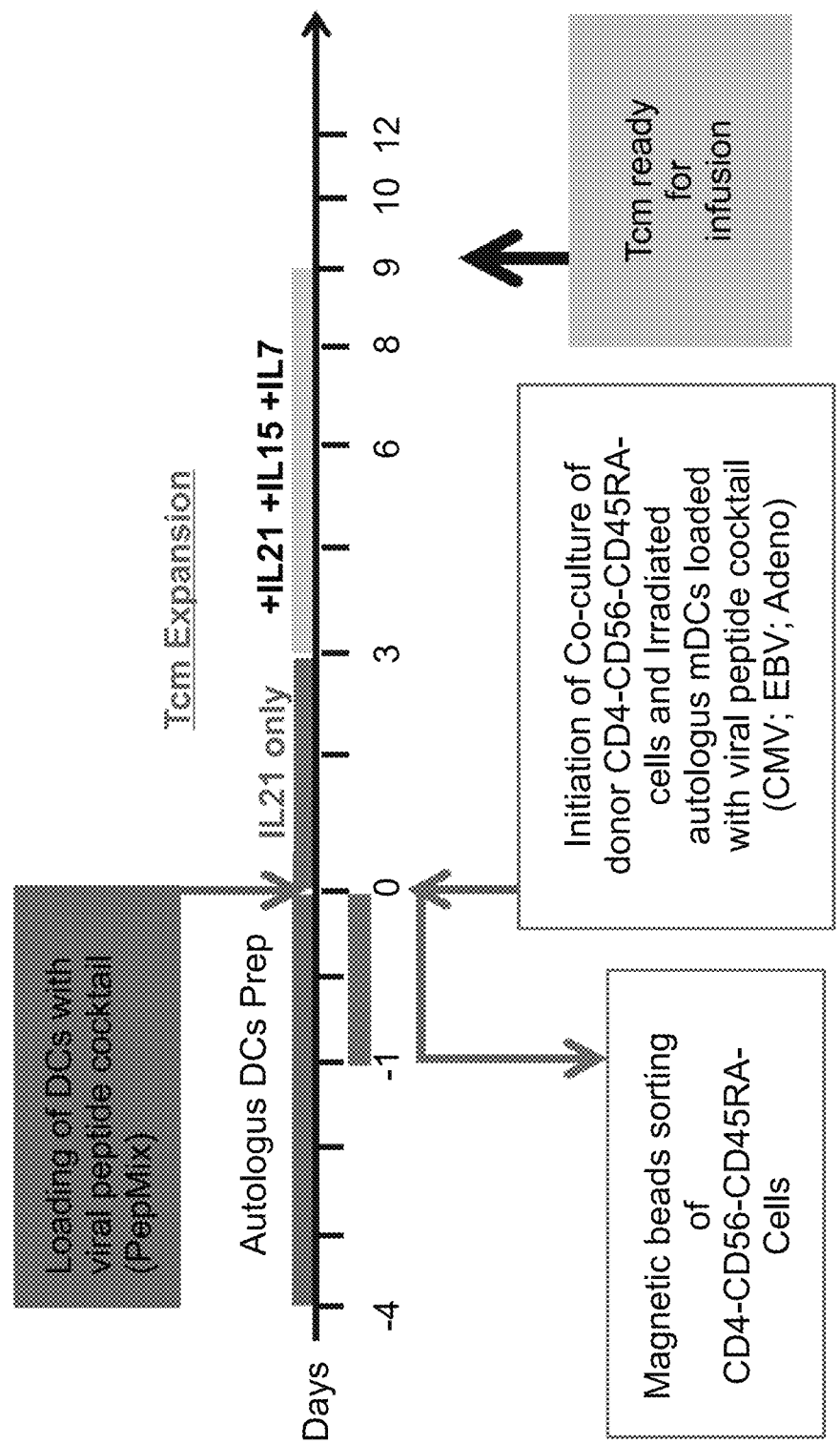
FIG. 7 is a schematic representation of an embodiment of a protocol for generation of human veto Tcm cells derived from memory T cells and cultured against viral antigens in the context of autologous antigen presenting cells.
Figure 9A:
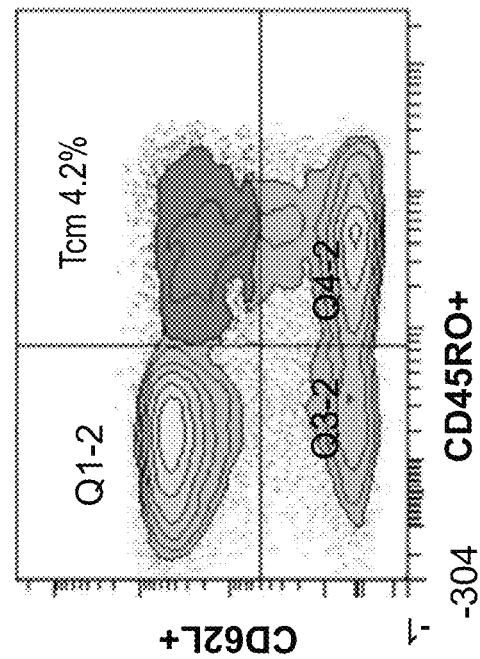
Figure 9B:
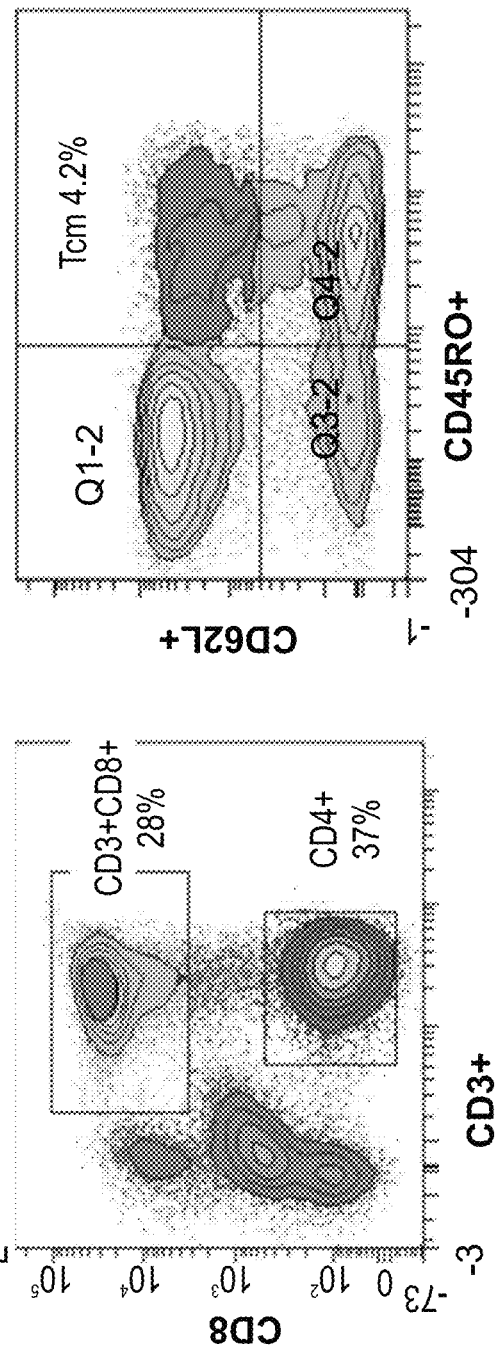
Figure 9C:
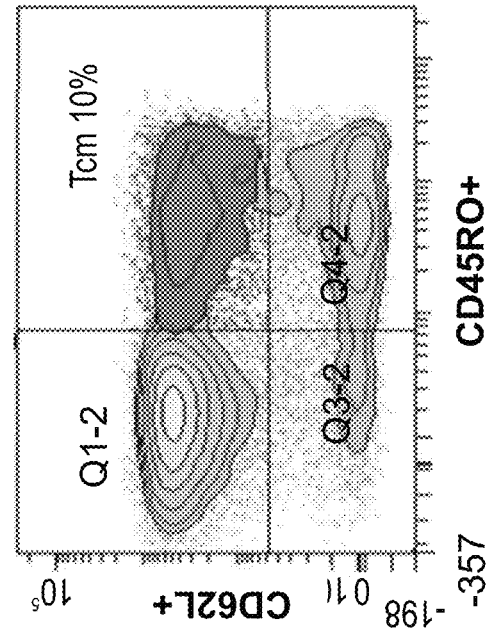
Figure 9D:
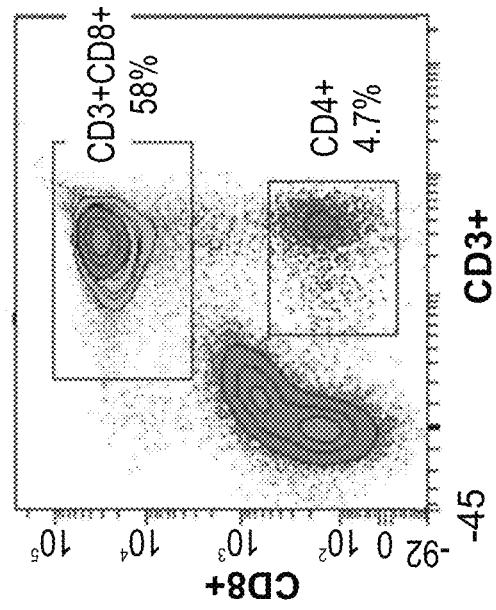

The present inventors have successfully repeated the protocol for generation of human veto cells from memory T cells using viral antigens presented on autologous antigen presenting cells for 10 times (FIG. 7). As can be seen in FIGS. 8 and 9A-9H, the cell recovery and purity of the novel protocol was very reproducible.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of generating an isolated population of non graft versus host disease (GvHD) inducing cells comprising a central memory T-lymphocyte (Tcm) phenotype, said cells being tolerance inducing cells and/or endowed with anti-disease activity, and capable of homing to the lymph nodes following transplantation, the method comprising:
    (a) providing a population of T cells comprising at least 70% memory T cells;
    (b) contacting said population of T cells with an antigen or antigens so as to allow enrichment of antigen reactive cells; and
    (c) culturing said cells resulting from step (b) in the presence of cytokines in an antigen free environment so as to allow proliferation of cells comprising said Tcm phenotype, thereby generating the isolated population of non-GvHD inducing cells.

2. The method of claim 1, wherein said memory T cells:
    are depleted of CD45RA$^+$ cells; and/or
    are depleted of CD4$^+$ and/or CD56$^+$ cells.

3. The method of claim 1, wherein said contacting said population of T cells with an antigen or antigens occurs in the presence of IL-21.

4. The method of claim 1, wherein said culturing said cells resulting from step (b) in the presence of cytokines comprises culturing said cells in the presence of any of IL-21, IL-15 and/or IL-7.

5. The method of claim 1, further comprising treating a cell donor with an antigen or antigens prior to said providing said population of T cells comprising said at least 70% memory T cells.

6. The method of claim 1, wherein said antigen or antigens is selected from the group consisting of a viral antigen or antigens, a bacterial antigen or antigens, a tumor antigen or antigens, an autoimmune disease related antigen or antigens, a protein extract, a purified protein and a synthetic peptide.

7. The method of claim 6, wherein said viral antigen or antigens are obtained from a virus selected from the group consisting of an Epstein-Barr virus (EBV), an Adenovirus (Adv), a cytomegalovirus (CMV), a BK virus, a Hepatitis virus, a Herpes simplex virus, a Human immunodeficiency virus (HIV), an Influenza virus, a Japanese encephalitis virus, a Polio virus, a Rabies virus, a Respiratory syncytial virus (RSV), a Rubella virus, a Smallpox virus, a Varicella zoster virus, a Rotavirus, a West Nile virus and a Zika virus.

8. The method of claim 1, wherein said antigen or antigens is presented by antigen presenting cells.

9. The method of claim 1, wherein said antigen or antigens is presented by autologous antigen presenting cells, non-autologous antigen presenting cells, artificial vehicles or artificial antigen presenting cells.

10. The method of claim 1, wherein said antigen or antigens is presented by antigen presenting cells of the same origin as said memory T cells.

11. A method of generating an isolated population of non-GvHD inducing cells comprising a central memory T-lymphocyte (Tcm) phenotype, said cells being tolerance inducing cells and/or endowed with anti-disease activity, and capable of homing to the lymph nodes following transplantation, the method comprising:
   (a) treating peripheral blood mononuclear cells (PBMCs) with an agent capable of depleting $CD4^+$, $CD56^+$ and $CD45RA^+$ cells, or with an agent capable of selecting $CD45RO^+$, $CD8^+$ cells, so as to obtain a population of cells comprising T cells enriched in memory T cells comprising a $CD45RO^+CD45RA^-CD8^+$ phenotype;
   (b) contacting said population of cells resulting from step (a) with an antigen or antigens in the presence of IL-21 so as to allow enrichment of antigen reactive cells; and
   (c) culturing said cells resulting from step (b) in the presence of IL-21, IL-15 and/or IL-7 in an antigen free environment so as to allow proliferation of cells comprising said Tcm phenotype, thereby generating the isolated population of non-GvHD inducing cells.

12. A method of generating an isolated population of non-GvHD inducing cells comprising a central memory T-lymphocyte (Tcm) phenotype, said cells being tolerance inducing cells and/or endowed with anti-disease activity, and capable of homing to the lymph nodes following transplantation, the method comprising:
   (a) treating peripheral blood mononuclear cells (PBMCs) with an agent capable of depleting $CD4^+$, $CD56^+$ and $CD45RA^+$ cells, or with an agent capable of selecting $CD45RO^+$, $CD8^+$ cells, so as to obtain a population of cells comprising T cells enriched in memory T cells comprising a $CD45RO^+CD45RA^-CD8^+$ phenotype;
   (b) contacting said population of cells resulting from step (a) with a viral antigen or antigens in the presence of IL-21 so as to allow enrichment of antigen reactive cells; and
   (c) culturing said cells resulting from step (b) in the presence of IL-21, IL-15 and/or IL-7 in an antigen free environment so as to allow proliferation of cells comprising said Tcm phenotype, thereby generating the isolated population of non-GvHD inducing cells.

13. The method of claim 12, wherein said viral antigen or antigens comprises an EBV peptide, a CMV peptide, an Adenovirus (Adv) peptide, and/or a BK virus peptide.

14. An isolated population of non-GvHD inducing cells generated according to the method of claim 1.

15. A pharmaceutical composition comprising as an active ingredient the isolated population of non-GvHD inducing cells of claim 14 and a pharmaceutical acceptable carrier.

16. A method of treating a disease in a subject in need thereof, the method comprising administering to the subject a therapeutically effective amount of the isolated population of non-GvHD inducing cells of claim 14, thereby treating the disease in the subject.

17. A method of treating a disease in a subject in need thereof, the method comprising:
   (a) analyzing a biological sample of a subject for the presence of an antigen or antigens associated with the disease;
   (b) generating an isolated population of non-GvHD inducing cells according to the method of claim 1 towards said antigen or antigens associated with the disease so as to allow enrichment of antigen reactive cells; and
   (c) administering to the subject a therapeutically effective amount of the isolated population of non-GvHD inducing cells of (b), thereby treating the disease in the subject.

18. A method of treating a subject in need of a cell or tissue transplantation, the method comprising:
   (a) transplanting a cell or tissue transplant into the subject; and
   (b) administering to the subject a therapeutically effective amount of the isolated population of non-GvHD inducing cells of claim 14, thereby treating the subject in need of the cell or tissue transplantation.

19. The method of claim 12, wherein said viral antigen or antigens comprises three EBV peptides, two CMV peptides and two Adenovirus (Adv) peptides.

20. The method of claim 12, wherein said viral antigen or antigens is/are selected from the group consisting of EBV-LNP2, EBV-BZLF1, EBV-EBNA1, CMV-pp65, CMV-IE-1, Adv-penton, and/or Adv-hexon.

21. The method of claim 12, wherein said viral antigen or antigens comprises two or more of EBV-LMP2, EBV-BZLF1, EBV-EBNA1, CMV-pp65, CMV-IE-1, Adv-penton and Adv-hexon.

* * * * *